(12) United States Patent
Widick

(10) Patent No.: US 11,629,323 B1
(45) Date of Patent: *Apr. 18, 2023

(54) SYSTEM FOR THE FORMATION OF FIBRIN FOAM

(71) Applicant: Mark H. Widick, Boca Raton, FL (US)

(72) Inventor: Mark H. Widick, Boca Raton, FL (US)

(73) Assignee: Fibrin, LLC, Delray Beach, FL (US)

(*) Notice: Subject to any disclaimer, the term of this patent is extended or adjusted under 35 U.S.C. 154(b) by 170 days.

This patent is subject to a terminal disclaimer.

(21) Appl. No.: 16/709,524

(22) Filed: Dec. 10, 2019

Related U.S. Application Data

(63) Continuation-in-part of application No. 15/262,157, filed on Sep. 12, 2016, now Pat. No. 10,501,715.

(60) Provisional application No. 62/217,460, filed on Sep. 11, 2015.

(51) Int. Cl.
| | |
|---|---|
| *C12M 3/00* | (2006.01) |
| *B01L 3/00* | (2006.01) |
| *C12M 1/26* | (2006.01) |
| *A61L 26/00* | (2006.01) |
| *C12M 1/00* | (2006.01) |
| *C12M 1/12* | (2006.01) |
| *A61J 1/05* | (2006.01) |

(52) U.S. Cl.
CPC ............... *C12M 33/10* (2013.01); *A61J 1/05* (2013.01); *A61L 26/0042* (2013.01); *A61L 26/0085* (2013.01); *C12M 23/34* (2013.01); *C12M 23/42* (2013.01); *C12M 25/18* (2013.01)

(58) Field of Classification Search
CPC ...... B01L 2400/0409; B01L 3/502753; C12M 47/02; C12M 45/05
See application file for complete search history.

(56) References Cited

U.S. PATENT DOCUMENTS

| | | | | |
|---|---|---|---|---|
| 5,585,007 A | * | 12/1996 | Antanavich | ............ B01D 61/18 494/36 |
| 6,143,247 A | * | 11/2000 | Sheppard, Jr. | ......... G01N 33/68 422/50 |
| 6,368,298 B1 | * | 4/2002 | Beretta | ................. A61L 24/106 604/4.01 |

(Continued)

*Primary Examiner* — Nathan A Bowers
(74) *Attorney, Agent, or Firm* — Barbara E. Johnson, Esq.

(57) ABSTRACT

A device and method for forming fibrin foam, preferably utilizing a single container, comprising a base structured to be rotationally driven and including a separation chamber disposed and structured to receive a blood sample therein. The base includes a reaction chamber disposed in fluid communication with said separation chamber. The blood sample is separated into a plasma segment and a packed cell segment when subjected to sufficient centrifugation concurrent to the driven rotation of the base. According to structural features, and in some instances concurrent and continuous centrifugation, the plasma segment is directed from said separation chamber into said reaction chamber which includes sufficient quantities of gas and reactant composition to facilitate formation of fibrin foam therein concurrent to centrifugation. Further centrifugation of the fibrin foam and the inclusion of additional features such as a pressurized reaction chamber facilitate the formation of fibrin foam exhibiting varying chemical and/or physical properties.

8 Claims, 13 Drawing Sheets

(56) References Cited

U.S. PATENT DOCUMENTS

| | | | | |
|---|---|---|---|---|
| 8,187,475 B2* | 5/2012 | Hecker | ......... | C12Y 304/21005 210/660 |
| 8,337,711 B2* | 12/2012 | Dorian | ................. | B01L 3/5021 422/527 |
| 8,753,670 B2* | 6/2014 | Delmotte | ......... | B01F 33/50112 604/82 |
| 2015/0138567 A1* | 5/2015 | Huang | ................. | B01L 3/5027 494/10 |

* cited by examiner

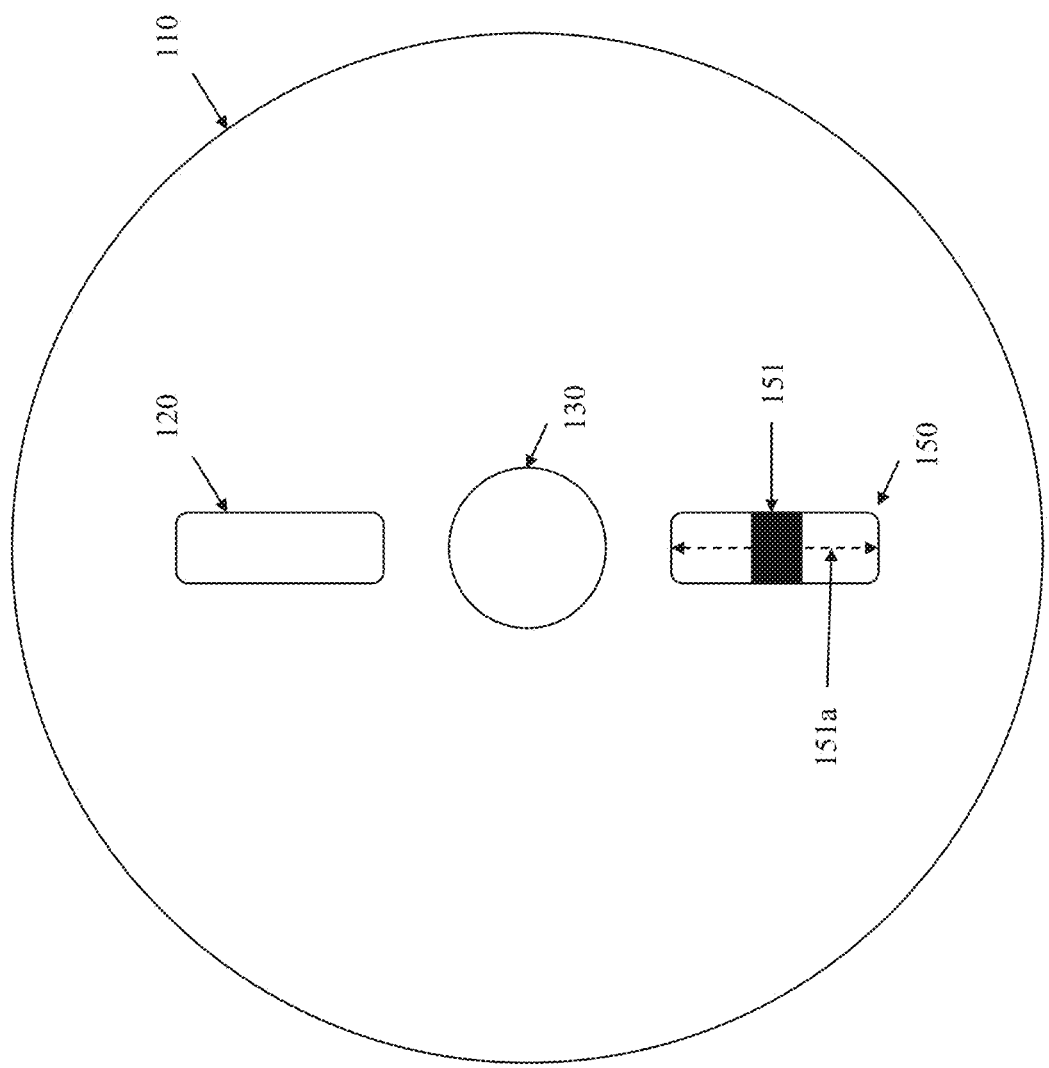

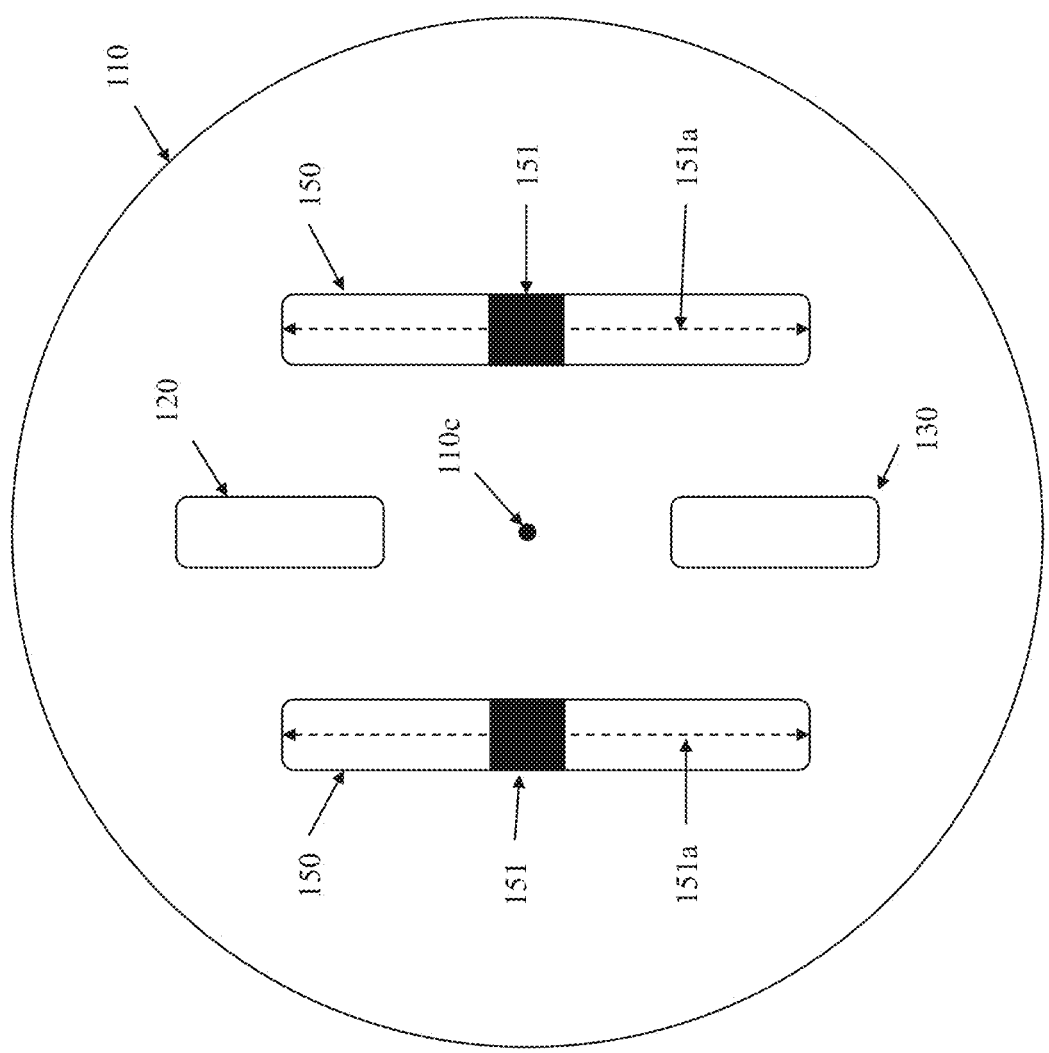

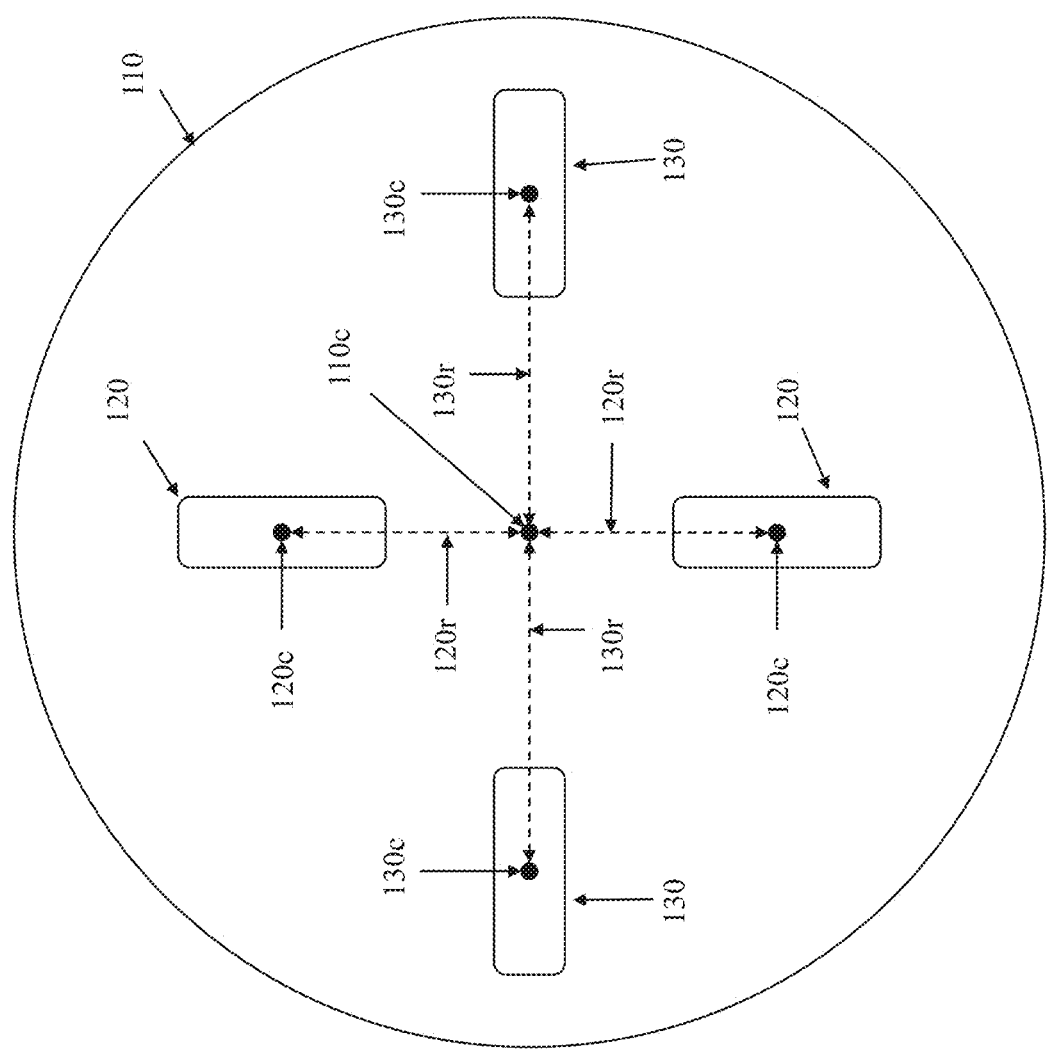

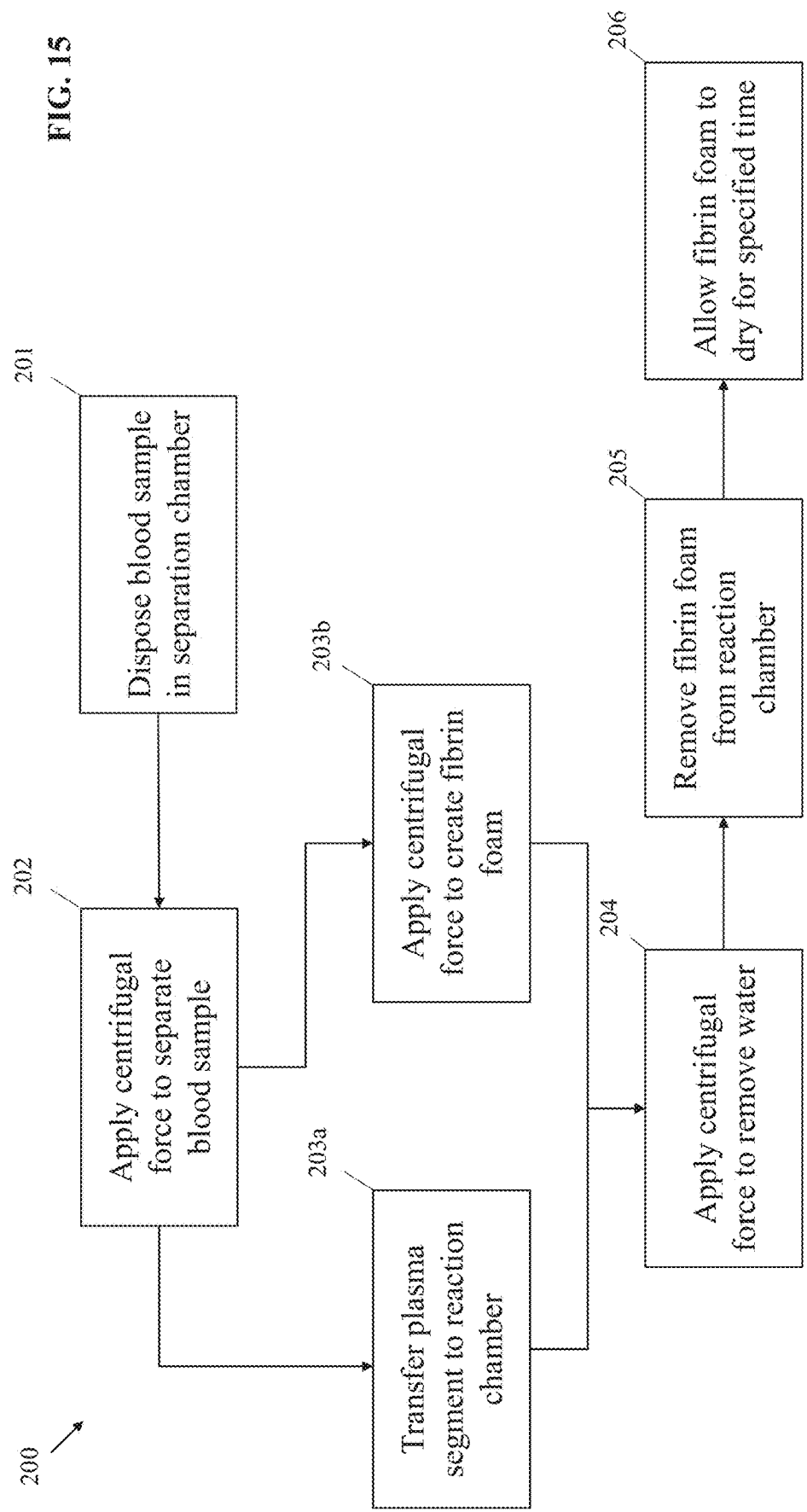

SYSTEM FOR THE FORMATION OF FIBRIN FOAM

CLAIM OF PRIORITY

This Continuation-in-part patent application hereby makes a claim of priority to an earlier filed and currently pending U.S. Non-Provisional patent application having application Ser. No. 15/262,157 and a filing date of Sep. 12, 2016, which itself claims priority to an earlier filed U.S. provisional patent application having Ser. No. 62/217,460 and a filing date of Sep. 11, 2015, both of which are incorporated herewith in their entireties.

BACKGROUND OF THE INVENTION

Field of the Invention

The present invention is directed to a device and method for the formation of fibrin foam in a quick and efficient manner, and may be capable of forming fibrin foam while a surgical procedure is underway. In one embodiment, the device and method forms fibrin foam within a single container associated with a base that is structured to be centrifuged by or as part of a rotational drive assembly. Centrifugation of the base results in separation of a blood sample into at least a plasma segment and a packed cell segment, with thereafter, the plasma segment directed into a reaction chamber associated with the base. The reaction chamber contains sufficient quantities of gas and a reactant composition to facilitate the formation of fibrin foam or corresponding fibrin products, also while centrifugation of the base occurs.

DESCRIPTION OF THE RELATED ART

Numerous procedures have been attempted in an effort to create and/or form tissue sealants, adhesives, films, foam matrices, etc. applicable for use in surgical procedures. Known tissue supplements include natural fibrin glues, sealants, etc. made from blood components. Surgical fibrin components may be made up from human fibrinogen activated by a thrombin-like enzyme such as thrombin itself or any other material with a similar activity. Such fibrin components have been shown to be superior to similar synthetic components for use in traditional surgery in many different situations. Accordingly, it is recognized fibrin glue, sealants, foam, etc. and like fibrin products have many advantages over related or corresponding synthetic components for surgical use.

Currently, such fibrin components are made by isolating a concentrate of human fibrinogen, such as by cryoprecipitation, and combining it before use with a bovine or human thrombin, as generally set forth above. The thrombin enzyme converts the fibrinogen to fibrin which rapidly gels into a foam, film or like consistently textured matrix. Similarly, the most common method of application of fibrin components include the mixing of concentrated fibrinogen from pooled human blood with a thrombin enzyme and calcium immediately before use.

However, few, if any, known or existing methods or procedures are readily adaptable for the convenient and efficient use of an autologous plasma fraction which can be prepared quickly during a surgical procedure. As is commonly recognized, autologous blood products are superior for safety and biocompatibility reasons. More specifically, known and existing prior art procedures for the formation of fibrin tissue supplements utilizing the preparation of a fibrinogen containing fraction for this purpose are time-consuming and frequently too complex to be completed in a short enough time to be accomplished during the surgical procedure. Also, known procedures frequently involve the use of complicated, specialized equipment, which also presents problems with the efficient creation of fibrin foam or like fibrin products.

To overcome such disadvantages and problems, attempts have been made to prepare fibrin compositions for a patient in advance of a surgical procedure. However, this imposes an undesirable need or requirement of utilizing additional procedures for identification and retrieval of the particular blood sample, that matches with a given patient. This, in turn, creates an opportunity for error, besides inconvenience, at least to the extent of requiring additional time, appointments, etc. of both the patient and corresponding medical personnel. It should also be apparent that such preparatory procedures are not possible when a surgical procedure must be performed on an emergency basis.

Finally, some known procedures exist but involve the use of complicated, specialized equipment. Such equipment can require specific manufacturing processes and the use of such specialized equipment commonly raises the cost associated with the efficient creation of fibrin foam or like fibrin products, particularly where such systems are predisposed to mechanical fatigue and failure.

Therefore, there is a need in the medical profession and especially, but not exclusively, in the surgical arts for an efficient, quick and effective system, including a device and associated methods, for the formation of a fibrin product including, but not limited to, a fibrin foam matrix. If any such system, device or method were developed, it should allow for the formation of a fibrin foam or like fibrin component in the operating room, concurrently during the performance of a surgical procedure, and ideally using the patient's own blood. Of course, if any such system were developed, it may also facilitate the formation of a fibrin foam or like fibrin product from a non-autologous blood sample, such as an allogeneic donor blood sample or plasma component.

Additionally, if any such system or device were developed, it would ideally be accomplished as part of or within a single container, so as to facilitate the process and further, avoid complex structural components that tend to be subject to incidents of mechanical failure, such as those resulting from system imbalance or fatigue. Moreover, any such system, device and/or method, and corresponding structural components should seek to use standard medical equipment, thereby reducing the initial costs, as well as operating and repair costs of operating such a system.

Finally, if any such system, device and/or method were developed, it should allow for the creation of specifically tailored fibrin components. For instance, the creation of fibrin foam and/or fibrin products could potentially be made with varying physical properties, such as density, to allow for the more effective application of said components in various anatomical regions of the human body.

SUMMARY OF THE INVENTION

The present invention is intended to address and present a solution to these and other long felt needs that remain in this field of art. Accordingly, the present invention is directed to a system, device and/or method for the formation of fibrin foam or other fibrin products in a quick and efficient manner. As such, most embodiments of the invention are particularly well suited for use while a patient undergoes surgery, so that the fibrin foam being produced can be used in or on the patient, as needed.

According to the invention, fibrin foam or anther fibrin product is formed with a device that comprises or includes a single container, such as but not limited to a cartridge or vial, which is subjected to centrifugation. A patient's blood sample is introduced to the device and following centrifugation, results in the separation of the blood sample into at least a plasma segment and another segment (erythrocytes) that is red in color and which contains most of the red blood cells. For purposes of clarity, the mostly red blood cell segment (erythrocytes) may be referred to herein as a "packed cell" segment and is distinguished from the "plasma segment" and a "buffy coat" segment, which may comprise a fraction of anticoagulated blood containing most of the white blood cells and platelets, as previously discussed. Subsequent to separation, the plasma segment is further processed, and/or as described more in detail subsequently herein, transferred to a reaction chamber or reaction assembly wherein, and while undergoing additional centrifugation, a fibrin foam or other fibrin product is formed. Accordingly, the fibrin foam or other fibrin product may be quickly and efficiently produced while a surgical procedure is being performed, in which the produced fibrin foam product may be used.

More specifically, the invention comprises in one embodiment a container for the formation of the fibrin foam or other fibrin product which is structured to be rotationally driven. The container, which may comprise but is not limited to a cartridge<includes a primary chamber disposed and structured to receive a blood sample therein. The cartridge may be removably connected to a rotational drive assembly, such as a centrifuge, or otherwise be at least partially integrated into the centrifuge or rotational drive assembly. Further, the container, whether in the form of a cartridge or otherwise, includes at least a reaction chamber and in certain additional embodiments, may include both a reaction chamber and a cell chamber. Upon at least an initial centrifugation, sufficient centrifugal force is exerted on or applied to the blood sample to facilitate its separation into at least the aforementioned plasma segment and a packed cell segment. In addition, the centrifugation may also result in the separation of a "buffy coat" segment from both the plasma and packed cell segments, as explained in greater detail hereinafter.

According to at least one embodiment of the invention, due at least in part from the application of sufficient centrifugal force on the blood sample, following separation of the plasma segment from the remainder of the blood sample occurs, the plasma segment will pass independently from the primary chamber into the reaction chamber for additional processing and the formation of the fibrin foam or other fibrin product. As also explained hereinafter, such additional processing may comprise the mixing of the separated plasma segment with a gas such as, but not limited to, air already existing in the reaction chamber. In addition, the plasma segment is concurrently mixed with a reactant composition also contained or otherwise introduced into the reaction chamber. The reactant composition is provided in sufficient quantity to facilitate coagulation concurrent to the mixing of the plasma segment with the air or other gas. Accordingly, the reactant composition may take the form of a thrombin or thrombin-like enzyme and calcium. Numerous factors are known to initiate or promote the conversion of fibrinogen to fibrin. Therefore, any one or more of a number of such factors or substances may be included in the reactant composition to allow for or if sufficient activity in the conversion reaction is present to create a fibrin matrix product having useful physical properties.

In one or more additional preferred embodiments, the gas maintained or introduced into the reaction chamber may be oxygen or air with an increased concentration of oxygen, given that oxygen is generally known to facilitate healing. The resulting fibrin foam or other fibrin product may be further enhanced by the addition of other agents such as, but not limited to, growth stimulants, hormones, cellular elements, bone, liver, skin, cartilage, chondroitin, platelets or other a predetermined parts of the body with which the resulting fibrin foam product is intended for use. In addition, artificial organs may benefit from a fibrin foam matrix to add cellular support.

As set forth above, the container, whether in the form of a cartridge or otherwise, may include a plurality of chambers including, but not limited to, the aforementioned primary chamber and reaction chamber. As such, subsequent to separation of the blood sample into at least a plasma segment and the packed cell segment and concurrent to centrifugation, in at least one embodiment the plasma segment will be forced through an appropriately structured passage into the reaction chamber for processing. Concurrently, a substantially equivalent centrifugal force will be applied to the separated packed cell segment of the blood sample. In order to avoid or at least minimize passage of a portion of the packed cell segment into the reaction chamber, it may be removed from the interior of the primary chamber to an exterior thereof. Therefore, in at least one preferred embodiment, the packed cell segment is directed from the interior of the primary chamber into the aforementioned cell chamber of the cartridge, concurrent to the passage of the plasma segment from the primary chamber into the reaction chamber.

It should be apparent that adequate centrifugation of the container and/or cartridge results in the development of sufficient centrifugal force to cause the separation of the blood sample into at least the plasma segment and the packed cell segment, as indicated. Further, and in at least one embodiment, the resulting centrifugal force should be sufficient to direct substantially all of the plasma segment into the reaction chamber concurrently to substantially all of the packed cell segment being directed out of the interior of the primary chamber, such as into the aforementioned cell chamber.

The possibility is recognized that a very minimal portion of the packed cell segment might also be passed into the reaction chamber. Accordingly, the structural features of the container and/or cartridge, including the cooperative disposition and structuring of the primary, reaction and cell chambers are such as to minimize inadvertent or undesirable mixing of the plasma segment and packed cell segment prior to or within the reaction chamber. More specifically, in at least one embodiment, the primary chamber may be substantially centrally located on or within the container, to the extent that the reaction chamber and the cell chamber are disposed in outwardly, substantially laterally surrounding relation to the primary chamber. As a result of this relative disposition, the development of sufficient centrifugal force during centrifugation will facilitate the passage of the plasma segment into the reaction chamber, as well as a removal of the packed cell segment from the interior of the primary chamber. Further, in at least one embodiment as described herein, each of the reaction and cell chambers is disposed in independent fluid communication with the primary chamber by virtue of the provision of a plurality of corresponding passages disposed and/or extending therebetween. As such, the reaction chamber and the cell chamber are separated to avoid direct fluid communication therebetween. The absence of fluid communication between the reaction chamber and the cell chamber prohibits or at least restricts a mixing of the plasma segment and packed cell segment with one another in either of the reaction chamber and cell chamber.

Therefore, the container and/or cartridge includes at least a first passage disposed and structured to facilitate flow of the plasma segment from the primary chamber into the reaction chamber, concurrent to the driven rotation and centrifugation. In at least one embodiment, the container and/or cartridge also includes at least a second passage disposed and structured to facilitate flow of the packed cell segment from the interior of the primary chamber to an exterior of the primary chamber. In one or more embodiments of the cartridge which incorporate both the reaction chamber and a cell chamber, the packed cell segment is directed through the second passage into the interior of the cell chamber. Substantially at the same time, the plasma segment is directed or forced, by the presence of centrifugal force, through the first passage into the reaction chamber. Accordingly, the passage of the plasma segment and the packed cell segment respectively and independently into the reaction chamber and the cell chamber occurs while the cartridge is being rotationally driven to establish the intended and desired centrifugal force present during centrifugation of the cartridge.

Additionally, in at least one embodiment of the invention, the container and/or cartridge may include a valve structure associated with at least the first passage and positionable between closed and opened orientations. The valve structure assumes a closed orientation during at least the initial centrifugation and until separation of the blood sample has separated into the plasma and packed cell segments. Subsequent to such separation, the valve structure may be either manually or "automatically" positioned into the open orientation, by a valve actuator. As set forth in greater detail hereinafter, the valve actuator may be manually operated or actuated based on visual observation of the separation of the blood sample within the interior of at least the primary chamber. In addition, the valve actuator may be operated/activated "automatically" by a determination of separation of the blood sample within the primary chamber. Such "automatic" actuation of the valve actuator may occur through the provision of a photo-sensor assembly or like structure, a time-based activating assembly, a speed based (RPM sensor) activating assembly, or the like. Further, the valve actuator may comprise a solenoid assembly operatively connected to accomplish the disposition of the valve structure between the open and closed orientations.

As at least one alternative embodiment, the valve structure may be connected to or incorporated within the container and/or cartridge in the form of a pressure relief valve. Operation thereof would be based on the development of sufficient centrifugal force to position the pressure relief valve from a biased, normally closed orientation into an open orientation. The amount of centrifugal force required to dispose the pressure relief valve in an open orientation may be greater than that to cause a separation of the blood sample into at least the plasma segment and the packed cell segment. More specifically, a first predetermined centrifugal force may be applied to the container and/or cartridge by centrifugation, which would be sufficient to cause a separation of the blood sample into the plasma segment and the packed cell segment. Once such separation has been determined, an additional, increased predetermined centrifugal force may be applied to the c container and/or cartridge, by a continued centrifugation, in order to open the pressure relief valve, allowing the plasma segment to pass from the primary chamber into the reaction chamber.

As indicated, the manual or automatic operation/activation of the valve actuator, resulting in positioning of the valve structure in an open orientation, is accomplished upon a determination that the initial blood sample has in fact separated into at least the plasma segment and the packed cell segment. As further indicated, the separation of the blood sample and the passage of the plasma segment and the packed cell segment out of the primary chamber occurs during centrifugation and is based on sufficient centrifugal force being exerted on the cartridge.

Yet additional features associated with one or more preferred embodiments of the present invention is the inclusion of a mixing structure disposed at least partially within and/or contiguous the entrance to the reaction chamber. Such mixing structure may assume different sizes, configurations and locations and is disposed in at least partially interruptive relation to the flow of the plasma segment into and/or within the reaction chamber. Such interruptive engagement with the plasma segment flow results in the creation of turbulence and/or a turbulent flow of the plasma segment as it enters the reaction chamber and/or is present therein. Such turbulence will in turn result in an enhanced mixture of the air or other gas and the reactant composition within the reaction chamber.

One or more embodiments of the present invention also contemplate the utilization of a stabilizing member or structure disposed within the interior of the primary chamber so as to movably interact with the blood sample, at least initially, during centrifugation. The position and/or movement of the stabilizing member may be defined as a substantially "free movement" by not directly connecting the stabilizing member to interior portions of the primary chamber. Accordingly, moving interaction with the stabilizing member and the blood sample, during centrifugation, restricts the formation of disruptive pooling, collective grouping or other undesirable migration of the blood sample within the primary chamber, to the extent that separation thereof into the plasma and packed cell segments is not hampered. Such an undesirable collection, grouping or pooling, etc. of the blood sample within the primary chamber may be the result of vibration, initial uneven rotation of the canister or other factors. The movable interaction of the stabilizer member with the blood sample serves to substantially or at least partially evenly distribute the blood sample within the primary chamber and thereby facilitate separation thereof into at least the plasma segment and the packed cell segment.

In at least one embodiment, the present invention is also directed to a method of forming fibrin foam or fibrin product(s), utilizing the structural components set forth herein, from a plasma segment separated from a blood sample during centrifugation. The inventive method preferably achieves the formation of fibrin on a single device, or within a single container. Moreover, at least one preferred method of application includes the utilization of a cartridge structured to be rotationally driven and which includes at least a primary chamber and a reaction chamber, wherein a cell chamber may also be included as part of the canister. The blood sample is enclosed within the primary chamber and the cartridge and is subjected to centrifugation, through the driving rotation thereof, sufficient to separate the blood sample into at least the plasma segment and a packed cell segment. Once separated, the plasma segment is directed from the primary chamber through at least a first passage into the reaction chamber, also while under centrifugation of the container and/or cartridge, according to at least one embodiment. Substantially concurrently, the packed cell segment may be directed along a second passage from the interior of the primary chamber to an exterior thereof, according to another embodiment. As such, the packed cell segment, subsequent to separation may be directed from the interior of the primary chamber into the interior of the cell chamber for collection and possible further use.

Upon passing of the plasma segment into the reaction chamber, it is mixed with a sufficient quantity of air or other appropriate gas composition and a coagulating reactant composition, concurrent to continued centrifugation resulting in the formation of the fibrin foam or other fiber product.

Additional features which may be incorporated in the present invention include the forming of the fibrin foam into a matrix or one or more different structural configurations. More specifically, it is further contemplated that the resulting fibrin foam formed in the reaction chamber may be subsequently forced therefrom through an apertured outer barrier, partition or wall during centrifugation. As such passage of the fibrin foam, through a plurality of apertures of predetermined size, configuration and disposition will result in the formation of a plurality of thin fibrin "threads". In turn, the collection of such threads may be blended, twisted or otherwise formed into more practically usable items such as suture material or the like. This additional feature of forming "fibrin threads" is at least minimally similar to the formation of "cotton candy" wherein spun sugar is formed in thin thread like components and collected on an exterior "catch" wall where it may be collected and shaped into a more useable form, object, etc. Therefore, it should be apparent that the advantages of the present invention, including the various preferred embodiments thereof, results in the formation of a fibrin product capable of assuming different sizes, configurations, formats, matrices, etc. thereby enhancing the utilitarian versatility the resulting fibrin foam product being formed.

Yet additional features associated with one or more preferred embodiments of the present invention is the inclusion of a mixing structure disposed at least partially within and/or contiguous the entrance to the reaction chamber. Such mixing structure may assume different sizes, configurations and locations and is disposed in at least partially interruptive relation to the flow of the plasma segment into and/or within the reaction chamber. Such interruptive engagement with the plasma segment flow results in the creation of turbulence and/or a turbulent flow of the plasma segment as it enters the reaction chamber and/or is present therein. Such turbulence will result in an enhanced mixture of the plasma segment with the air or other gas and the reactant composition within the reaction chamber.

The present invention may comprise, however, other embodiments. For example, in one additional and more preferred embodiment of the invention, a container for the formation of fibrin foam or other like fibrin product may comprise a base structured to be rotationally driven according to at least partial connection to, or integration into, a rotational drive assembly, such as a centrifuge. The base may include a separation assembly, such as a cartridge, a syringe, a canister or a vial, disposed and structured to receive a blood sample therein. The separation assembly may comprise at least one, and in some embodiments a plurality, of separation chambers, such as syringes or other like chambers, tubes, or components, which may, in some embodiments, be removably connected to the base. Further, the base may include a reaction assembly comprising at least one reaction chamber. Upon at least an initial phase of centrifugation, sufficient centrifugal force is exerted on or applied to separation assembly and the blood sample within it, to cause the blood sample to separate into at least the aforementioned plasma segment and packed cell segment. Additionally, the centrifugation may also result in the separation of a buffy coat segment from both the plasma segment and packed cell segment, as previously described.

As may be understood, for the effective creation of fibrin foam, the plasma segment and the packed cell segment must be sufficiently separated from the blood sample. In order to ensure sufficient separation, it may be understood the amount of time required for a complete separation at a given rotational speed may be determined according to the patient's hematic profile. Accordingly, in alternative embodiments of the present invention, the device may be rotationally driven at a given rotational speed for a certain amount of time, a predetermined number of rotations, or a certain amount of distance travelled. Accordingly, the device may be manually or electrically predisposed to signal an end or ending of the blood sample's separation phase after the occurrence of one of the aforementioned predetermined events.

Subsequent to separation of the plasma segment from the remainder of the blood sample, the plasma segment will pass from the primary chamber into the reaction chamber for additional processing into the fibrin foam or like fibrin product. As previously explained, such additional processing may comprise the mixing of the separated plasma segment with a gas, such as, but not limited to, air already existing in the reaction chamber. Further, the plasma segment is concurrently mixed with a reactant composition also contained in, or otherwise introduced into, the reaction chamber. The reactant composition is provided in sufficient quantity to facilitate coagulation concurrent to the mixing of the plasma segment with the air or other gas. Accordingly, the reactant composition may take the form of a thrombin or thrombin-like enzyme and calcium. As may be known, because numerous factors may initiate or promote the conversion of fibrinogen to fibrin, any one or more of a number of such factors or substances may be included in the reactant composition if sufficient activity in the conversion reaction is present to create a fibrin matrix product having useful physical properties.

As set forth above, in at least one alternative embodiment of the invention comprising a base, it may further include a plurality of separation chambers disposed thereon for the receipt of an additional blood sample. Further, the base may include at least one reaction chamber. As described subsequently herein, however, in some embodiments the number of separation chambers and reaction chambers disposed on the base may be equal. Moreover, as may be understood, due to the application of centrifugal force to the base, the plurality of separation chambers and the at least one reaction chamber should preferably be disposed in a counterbalancing relation, such that the distributed weight from the aforementioned structural components is disposed to maintain a center of mass located at the center of the base. Accordingly, in so doing, the base may be rotationally driven at varying rotational speeds without becoming unbalanced.

As may be further understood, as a result of the transfer of fluid during centrifugation, the possibility of system imbalance is realized. More specifically, there remains a possibility the device may become imbalanced as a result of the dynamic movement of the mass disposed therein.

Accordingly, in at least some embodiments of the present invention, a balancing system may be employed on the base and disposed in connection with the separation assembly and reaction assembly in order to maintain the balance of the device. Such a balancing system may comprise, for example, a vibration detector in connection with a logic board for measuring the inertia of the device. Further, such a vibration detector may be disposed in connection with various structural elements in order to adjust the balance in the device to maintain a specified level of inertia. For instance, such a structural element may comprise, without limitation, a movable weight disposed to counteract any mass displacement, or an actuation device disposed in connection with each of the plurality of separation chambers to individually drive additional fluid out of the separation chamber. Accordingly, use of such a balancing system in certain embodiments may allow the device to remain balanced and thereby effectively and efficiently produce fibrin foam while simultaneously reducing incidents of mechanical fatigue and failure.

Further, as previously mentioned, upon the separation of the blood sample into at least the plasma segment and the packed cell segment, the plasma segment will be transferred to the reaction chamber for additional processing. In at least one embodiment, the plasma segment will transfer due to the application of centrifugal force on the base. In alternative embodiments, the plasma segment may transfer to the reaction chamber at least in part due to the application of centrifugal force, or, without the application of centrifugal force as a result of the use of actuation devices, such as linear actuators or spring mechanisms. Moreover, in embodiments where the transfer of the plasma segment occurs without the application of centrifugal force, the separation assembly may be disposed at an incline so as to prevent the unintended combining or re-mixing of the plasma segment and the packed cell segment.

For example, in embodiments lacking an actuation device, centrifugal force may be continuously applied, possibly at varying rotational speeds, in order to effectuate the transfer of the plasma segment to the reaction chamber. In such an embodiment, the separation assembly and the reaction assembly may be disposed in a radial asymmetric orientation, such that the separation assembly is disposed closer to the axis of rotation of the base than the reaction assembly. Accordingly, as a result of the application of sufficient centrifugal force acting in concert with the radial asymmetry, a pressure differential will occur between the separation assembly and the reaction assembly, thereby creating a siphon effect acting upon at least the plasma segment and the packed cell segment. As may be understood, the siphon effect may initially act upon the less dense plasma segment, thus drawing this plasma segment to the reaction assembly, while the denser packed cell segment remains at the radial end of the separation assembly, at least in part due to the continuous application of centrifugal force. Further, and as may be understood, given sufficient time, the plasma segment should fully transfer to the reaction chamber and the denser packed cell segment will subsequently begin to transfer out of the separation chamber. As may be understood, application of sufficient centrifugal force may occur according to, for instance, a set time period or a manual input to change the rotational speed at which the base is driven.

Conversely, in embodiments comprising an actuation device, and typically without radial asymmetry between the separation chamber and the reaction chamber, transfer of the plasma segment to the reaction chamber may occur either with or without the application of centrifugal force. For instance, in one embodiment where the separation chamber comprises a syringe, the actuation device may comprise a lead weight connected to the body of the syringe. In such an embodiment, as centrifugal force is applied, the lead weight will be radially drawn, thereby forcing the body of the syringe towards the plunger, which may remain stationary, and thus forcing at least the plasma segment out of the tip of the syringe. Such an actuation device acting in concert with the separation chamber may beneficially prevent instances of "air lock," whereby air in the pathway connecting the separation chamber and the reaction chamber operates to prevent fluid transfer, because the resulting pressure increase from sliding the body of the syringe towards the plunger may overcome any such blockages. Conversely, in an alternative embodiment, the actuation device may comprise a spring assembly, such as, for instance, a spring, a release clip, and a stopper, whereby the release clip may be released, either automatically or manually, thereby effectuating the transfer of at least the plasma segment to the reaction chamber.

Alternatively, as may be understood, additional embodiments of the invention may comprise both the radial asymmetric placement of the separation assembly and the reaction assembly on the base, and the disposition of actuation devices on the separation assembly, as previously described. In such an embodiment, transfer of the plasma segment may occur as a result of both of the aforementioned structural features acting in concert, whereby the actuation device may be used to initially begin the transfer of the plasma segment by overcoming any minimal pressure requirements, while the pressure differential resulting from said radial displacement may help drive the remaining plasma segment into the reaction chamber. Alternatively, such an embodiment may instead involve a brief stop of the centrifugation force, while at lease an initial fluid transfer of the plasma segment occurs, before reapplying centrifugal force to the device.

In at least one embodiment, the invention can further comprise a divider assembly. As may be understood, the possibility of at least a minimal portion of the packed cell segment transferring into the reaction chamber may be avoided through the use of a divider assembly, which may be disposed on the base between the separation assembly and the reaction assembly. The divider assembly may comprise, for example, a valve structure, such as a check valve or burst pressure disc, disposed in connection with a filter. Accordingly, the check valve may be disposed in an open orientation upon the introduction of sufficient centrifugal force to meet the cracking pressure, thus allowing the passage of fluid, such as the plasma segment and the packed cell segment, towards the reaction assembly. Subsequent to passing through the check valve, the fluid will then pass through a filter disposed to prevent the passage of red blood cells. Accordingly, the plasma segment will flow through the filter and into the reaction chamber while the packed cell segment will become clogged at the filter and therefore prevented from passing into the reaction chamber.

As may be understood, additional and/or alternative structural elements may be employed to prevent the passage of the packed cell segment into the reaction chamber. For example, in alternative embodiments, a mechanical stopper may be user to prevent an excessive volume of fluid from exiting the separation assembly. The appropriate volume of fluid to transfer may be calculated according to the patient's known hematocrit, which may inform the physician of the volumetric percentage of red blood cells in the patient's blood. Accordingly, an appropriate volume for fluid transfer may be specified according to such a calculation.

Moreover, in certain embodiments, a sensing device, such as a colorimetric sensor or laser, may be employed to prevent the passage of the packed cell segment into the reaction chamber. As may be understood, such a sensing device may be employed in connection with a logic board to monitor the separation assembly and the transfer of fluid therefrom. Due to the difference in color between the plasma segment, which is typically a clear, yellowish fluid, and the packed cell segment, which is typically a dark red fluid, such a sensing device may determine when the plasma segment has fully transferred to the reaction assembly, such as by colorimetry. At such time, the sensing device may operate with associated mechanical structures, such as an actuator or mechanical stopper, to prevent the passage of the packed cell segment into the reaction chamber.

As previously stated, subsequent to the separation of the blood sample and the transfer of the plasma segment to the reaction chamber, the plasma segment will be mixed, also by way of centrifugal force applied to the base, with air or an alternative gas and the reactant composition disposed therein, for the formation of fibrin foam or other like fibrin product. Accordingly, upon mixture of the plasma segment with the aforementioned substances, a usable fibrin foam may be prepared. However, because fibrin foam or other like fibrin products may be characterized as a closed cell foam, meaning there will be no gas exchange with the fibrin foam's surroundings, various other procedural processes may be employed to further alter the chemical and physical properties of the fibrin foam or like fibrin product to more effectively tailor the fibrin foam being formed for a particular application in the human body.

For instance, as previously stated, in one or more additional preferred embodiments the gas maintained or introduced into the reaction chamber may be oxygen, or air with an increased concentration of oxygen, in order to produce a fibrin foam that is likely to facilitate healing. The resulting fibrin foam or other fibrin product may be further enhanced by the addition of any other therapeutic medical gas or other agents such as, but not limited to, growth stimulants, hormones, cellular elements, bone, liver, skin, cartilage, chondroitin, platelets or other predetermined parts of the body with which the resulting fibrin foam product is intended for use. In addition, artificial organs may benefit from a fibrin foam matrix to add cellular support. Alternatively, additional components may be disposed within the reaction chamber prior to the creation of the fibrin foam. For instance, an implant or other useful object may be disposed within reaction chamber for the fibrin foam to grow around, or the fibrin may be used as a carrier for a drug, such as a delayed release drug.

Moreover, in at least one additional embodiment, at least one reaction chamber may be pressurized prior to the mixing of the plasma segment with the air and reactant composition disposed therein. In such an instance, it may be understood the reaction chamber may first be pressurized prior to the initial centrifugation of the base for the separation of the blood sample. Alternatively, the reaction chamber may be pressurized as a result of the transfer of the plasma segment into the reaction chamber. For instance, by driving the plasma segment into the reaction chamber at increased pressure, either according to a greater centrifugal force or the force applied by an actuator, increased air will flood into the chamber, thereby increasing the pressure of the reaction chamber beyond atmospheric pressure to, for instance, two atmospheres of pressure. By doing so, subsequent to the formation and removal of the fibrin foam or like fibrin product, and according to the ideal gas law, the gas bubbles disposed within the fibrin foam will expand, thereby decreasing the density of the fibrin foam. As may be understood, by decreasing the density of the fibrin foam, additional and/or alternative physical properties may be imparted on the fibrin foam, such as reducing the thickness of the foam and thereby, likely imparting additional comfort for applications in small areas of the human body. Alternatively, as may be understood, the reaction chamber may be disposed at a pressure less than atmospheric pressure. In such an embodiment, upon the removal of the fibrin foam from the reaction chamber, the air bubbles disposed within the fibrin foam will instead shrink, thereby making a denser and more resilient fibrin foam, which may experience increased longevity.

Furthermore, the fibrin foam may additionally be altered as a result of extended and/or increased centrifugation during the fibrin foam formation step. For instance, additional centrifugation, such as by an extended period of centrifugation and/or centrifugation at an increased rotational speed, may remove any excess water disposed within the fibrin foam, thereby drying the fibrin foam prior to removal. As may be understood, dry fibrin foam has different physical characteristics than wet fibrin foam, such as being more elastic and adhesive, thus making dry fibrin foam preferable for certain applications. For instance, as may be understood, due to the physical space constraints of applying fibrin foam in certain applications, such as in the ear or nose, many of the aforementioned chemical and/or physical alterations to the fibrin foam are preferable. Accordingly, in at least one embodiment of the present invention, the reaction chamber may be pressurized beyond atmospheric pressure and the fibrin foam may be subjected to extended and/or increased centrifugation in order to create a fibrin foam or like fibrin product exhibiting certain chemical and/or physical properties, including, but not limited to, a lower density, reduced thickness, greater elasticity, and greater adhesiveness. Further, subsequent to the production of such a fibrin foam or like fibrin product, additional procedures may be employed, such as drying the fibrin foam or like fibrin product to further enhance such chemical and/or physical properties.

Moreover, additional embodiments may comprise reaction chambers of various sizes and shapes. As may be understood, the plasma segment, upon mixing with the reactant, may create a fibrin foam or like fibrin product disposed to be formed to the shape of the reaction chamber. Accordingly, a fibrin foam or like fibrin product may be sized and structured according to the specific constraints of its application.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 11 is a schematic illustration of one embodiment of the present invention including one separation chamber and one reaction chamber disposed in connection with a balancing system.

FIG. 12 is a schematic illustration of one embodiment of the present invention including one separation chamber and one reaction chamber disposed in connection with a balancing system.

FIG. 13 is a schematic illustration of one embodiment of the present invention including a plurality of separation chambers and a plurality of reaction chambers disposed in radial asymmetric orientation to one another.

FIG. 14 is a schematic illustration of one embodiment of the present invention including a plurality of separation chambers and a plurality of reaction chambers disposed in radial asymmetric orientation to one another with at least one divider assembly disposed there between.

FIG. 15 is a flow diagram of one embodiment of the present invention for the creation of fibrin foam with properties sufficient for application in the nose or ear.

Like reference numerals refer to like parts throughout the several views of the drawings.

DETAILED DESCRIPTION OF THE PREFERRED EMBODIMENT

Figure 1:
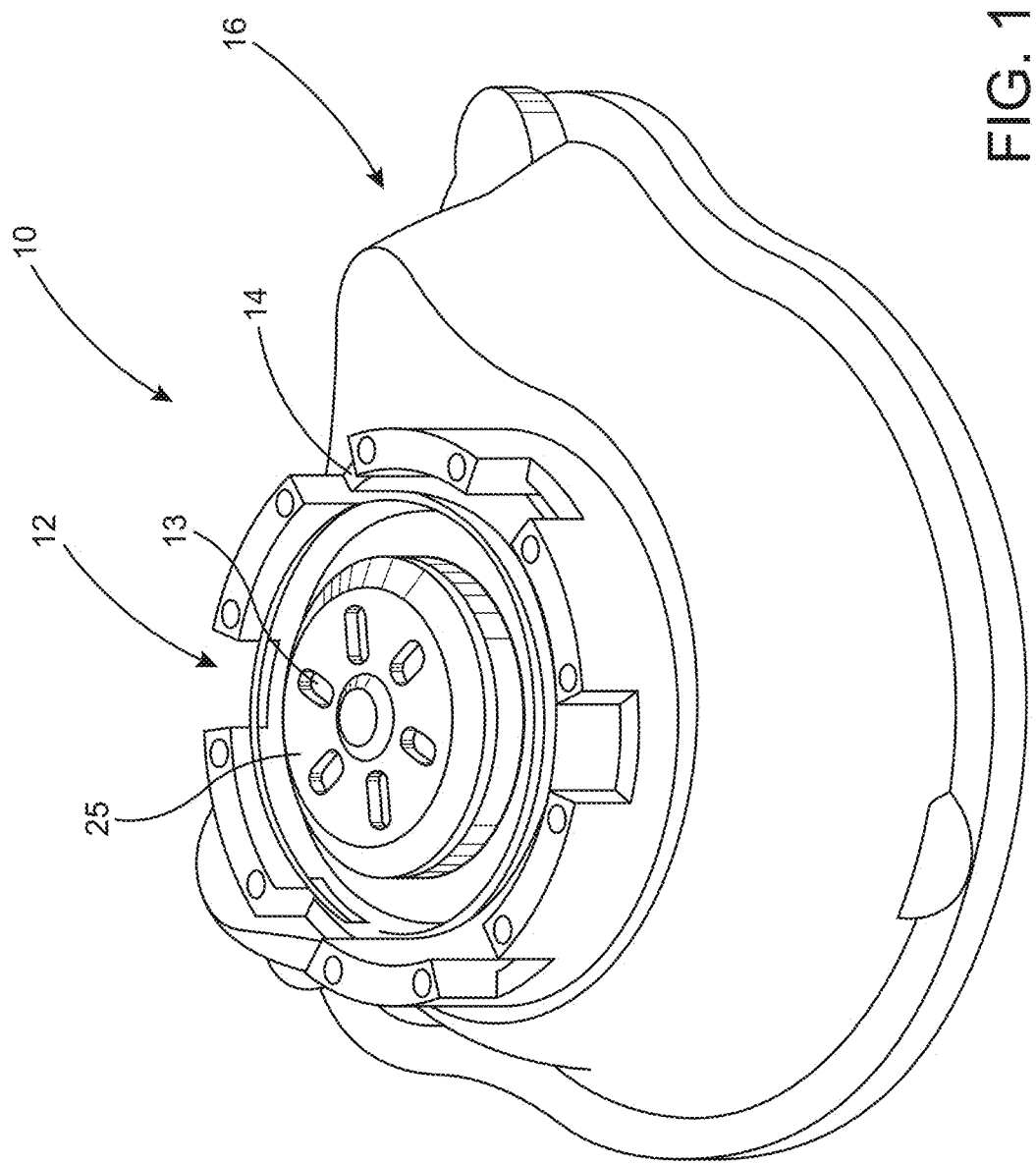
FIG. 1 is a perspective view of one embodiment of the present invention including a container connected to a centrifuge or like rotational driving assembly.

The present invention is directed to a system, device and/or method for the formation of fibrin foam or other fibrin products in a quick and efficient manner. As represented in the accompanying Figures and with initial reference at least to FIGS. 1 and 2, the system of the present invention is represented by a device having certain structures, generally indicated as 10, as well as an operatively associated method, representative of a practical application of the device and structure 10, as explained in greater detail hereinafter.

More specifically, the present invention includes the use of at least one container generally indicated as 12 including a cartridge or canister 14. The container 12 and cartridge or canister 14 are structured to be rotationally driven by a rotational drive assembly 16, which may be in the form of a centrifuge structure as explained in greater detail in FIG. 2. Further, the cartridge 14 may be removably connected in driven relation to the container 12 and rotational drive assembly or centrifuge 16 or may be at least partially integrated as a part thereof.

Figure 2:
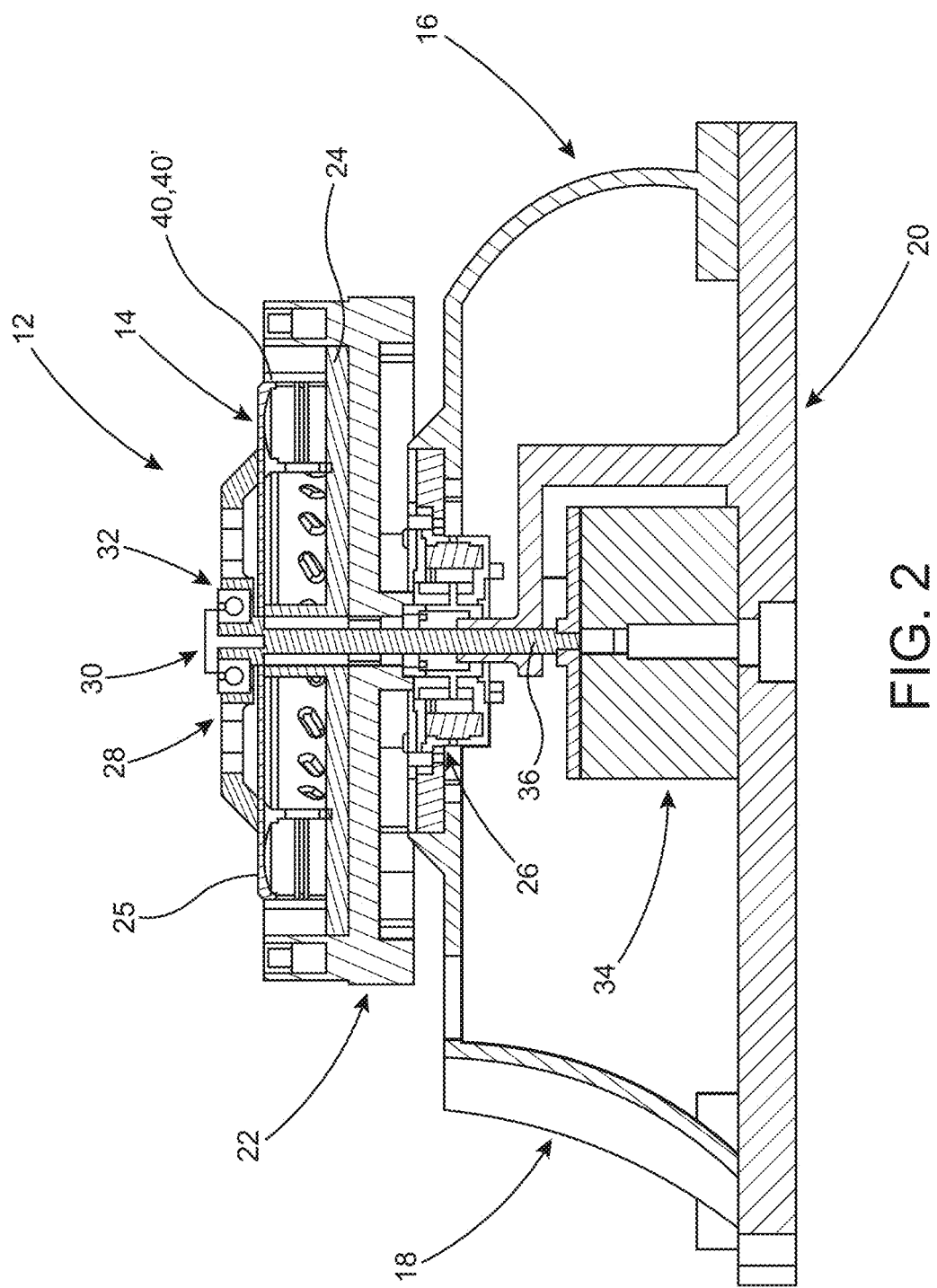
FIG. 2 is an interior, sectional view of the embodiment of FIG. 1.

As represented in FIG. 2, the rotational drive assembly or centrifuge 16 includes a housing 18 and a supporting base 20. Further, centrifuge 16 may also include a platform or "nest" 22 for support and driving interconnection with a base 24 of the canister 14. Therefore, when the canister 14 is disposed in an operative position, as represented in FIG. 2, it is drivingly connected to the rotational drive assembly or centrifuge 16 by virtue of its engagement with the nest or platform 22. In certain alternate embodiments, the nest or platform 22 may be considered a part of the canister 14 or a part of the centrifuge 16. In addition, the rotational drive assembly or centrifuge 16 includes a drive motor generally indicated as 26 appropriately mounted on the housing 18 so as to accomplish the intended driven rotation and centrifugation of the canister 14.

When operatively, but removably, connected to the centrifuge 16, the canister 14 includes a cover 25 which serves to cover an open end 40 of the canister 14 and close the interior thereof. Entry of a blood sample into the interior of the canister 14 and more specifically the primary chamber 42 may occur by passing through the opened end 40 or other inlet port or structure, dependent on the overall structural configuration of the canister 14. In addition, a closure device or "spider" cap 28 engages and effectively clamps the cover 25 down onto and in substantially sealing engagement with the outer periphery 40' of the open end 40 during centrifugation of the canister 14. Removable attachment of the cap 28 is accomplished by a connector 30, wherein a bearing assembly 32 serves to facilitate secure mounting of the cap 28 in clamping, closing relation to the cover 25 concurrent to forced rotation of the canister 14 during operation of the centrifuge 16.

In at least one preferred embodiment, a solenoid assembly 34 is provided preferably, but not necessarily, on the interior of the housing 18. The solenoid assembly 34 may be connected to the cap 28 by virtue of a shaft or spindle 36 passing through channel or opening 37 formed in the canister 14. Accordingly, upon activation of the solenoid assembly 34, the cap 28 is forced downwardly into a clamping engagement with the cover 25. Due to an at least partially flexible construction of the cover 25, a sealing engagement between the cap 25 and the periphery 40' of the open end 40 of the canister 14 will occur. In contrast, a second activation or release of the solenoid assembly 34 will at least slightly raise the cap 28, in turn resulting in a release of the sealing, clamping engagement between the cover 25 and the periphery 40' of the open end 40. As explained in greater detail hereinafter, the cap 28 and cover 25 may also be associated with a first passage 50 within the interior of the canister 14 facilitating transfer of a plasma segment, out of a primary chamber 42 within the canister 14.

Figure 3:
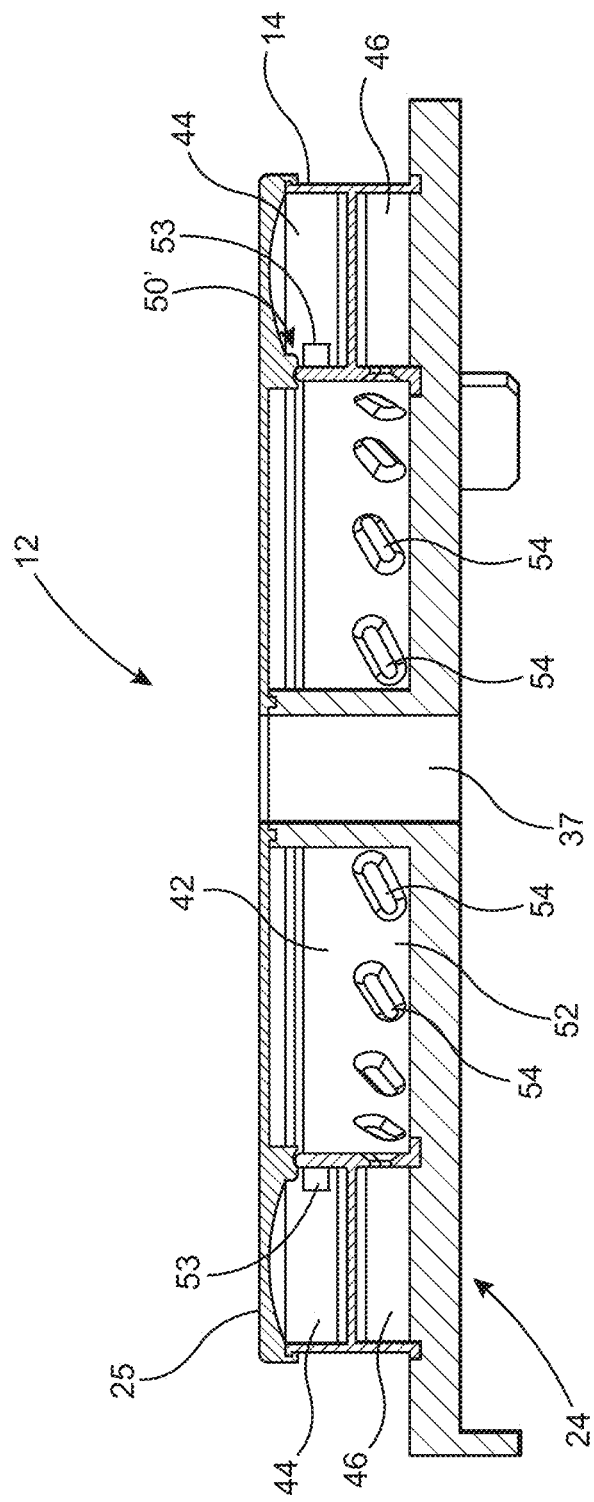
FIG. 3 is an interior sectional view of a container and canister associated with the embodiments of FIGS. 1 and 2.

Therefore, and with primary reference to at least FIGS. 2 and 3, the canister 14 of the container 12 includes the primary chamber 42 and at least a reaction chamber 44. In one or more preferred embodiments, as represented in at least FIGS. 3 and 4, the canister 14 also includes at least one cell chamber 46. As clearly represented, the primary chamber 42 is substantially centrally located within the interior of the canister 14. In cooperation therewith, the reaction chamber 44 and the cell chamber 46 are each located laterally and/or radially outward in substantially surrounding relation to the primary chamber 42 so as to take advantage of the centrifugal force developed during centrifugation of the canister 14. Moreover, during centrifugation sufficient, predetermined centrifugal force is exerted on a blood sample, placed within the primary chamber 42, to cause it to at least separate into the aforementioned plasma segment and packed cell segment.

Upon such separation of the supplied blood sample and during continued centrifugation, the plasma segment will pass from the primary chamber 42 into the reaction chamber 44 through at least a first passage 50. The first passage 50 is disposed between the upper periphery 40' of the open end 40 of the primary chamber 42 and an under surface or portion the cover 25, as at least partially explained above with primary reference to FIG. 2. Moreover, when the solenoid assembly 34 is activated to release clamping engagement with the cap 28 relative to the cover 25 the clamping sealing engagement between the cover 25 and the periphery 40' is released. This will facilitate passage of the separated plasma segment from an upper portion of the primary chamber 42, between the periphery 40' and the under portion of the cover 25 and through the first passage 50 into the interior of the reaction chamber 44, during the continued centrifugation of the canister 14 and the resulting development of subsequent centrifugal force on the contents of the canister 14.

Therefore, the opening and closing of the passage 50 as defined between corresponding portions of the cover 25 and upper, outer periphery 40' may define a valve structure 51 which either restricts or facilitates passage of the separated plasma segment from the interior of the primary chamber 42 through the first passage 50 into the interior of the reaction chamber 44. In this instance, the solenoid assembly 34 may be considered part of a valve actuator which serves to position the valve structure 51 (corresponding removably engaging portions of the cover 25 and periphery 40') between a closed orientation and an open orientation. Moreover, when the solenoid assembly 34 is activated to clamp the cap 28 downwardly onto the cover 25 the closed orientation of the valve 51 is established. In contrast, the open orientation of valve 51 is established upon an activation or release of the solenoid assembly 34 to release the cap 28 from clamping engagement with the cover 25 thereby serving to open the first passage 50 associated with the now open valve 51.

Figure 4:
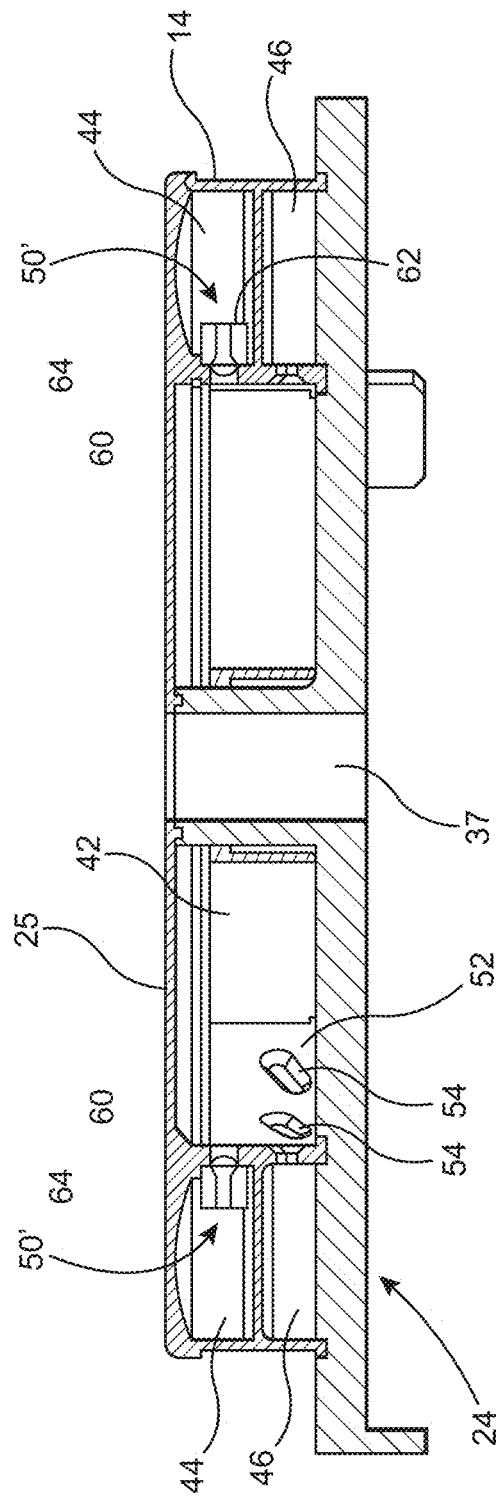
FIG. 4 is a sectional view of another embodiment of a container and canister which may be operatively associated with the embodiment of FIGS. 1 and 2.

As also represented in FIG. 3, the canister 14 includes a second passage at least partially defined by an internal barrier wall 52 disposed in surrounding relation to the primary chamber 42, and in at least partially segregating relation to the primary chamber 42 and the reaction and cell chambers 44 and 46 respectively. Further, the barrier wall 52 has an apertured construction more specifically defined by at least one but preferably a plurality of apertures 54 disposed in spaced relation to one another and collectively extending along a length of the curved barrier wall 52. It is to be noted that the one or more apertures 54 are located in a lower portion of the primary chamber 42 so as to be in substantially corresponding, fluid communicating relation to a packed cell segment of the blood sample subsequent to separation thereof from the plasma segment. The packed cell segment of the blood sample has a greater density and accordingly is "heavier" than the plasma segment. During centrifugation, the packed cell segment will therefore have a tendency to migrate towards the lower portion of the primary chamber 42 in alignment with the second passage at least partially defined by the one or more apertures 54. In the embodiment of FIGS. 3 and 4, the canister 14 is provided with a cell chamber 46. Accordingly upon centrifugation, the developed predetermined centrifugal force will direct or force the packed cell segment through the one or more apertures 54 out of the interior of the primary chamber 42.

When the cell chamber 46 is present and provided within the canister 14, the outwardly directed packed cell segment will pass into the interior of the cell chamber 46 for collection and possible further use.

Yet additional features associated with one or more preferred embodiments of the present invention is the inclusion of a mixing structure 53 disposed at least partially within and/or contiguous with the entrance into the reaction chamber 44. Such mixing structure(s) 53 may assume different sizes, configurations and locations and is disposed in at least partially interruptive relation to the flow of the plasma segment into and/or within the reaction chamber 44. Such interruptive engagement with the plasma segment flow results in the creation of turbulence and/or a turbulent flow of the plasma segment as it enters the reaction chamber 44 and/or is present therein. Such turbulence will in turn result in an enhanced mixture of the plasma segment with the air or other gas and the reactant composition within the reaction chamber.

Figure 5:
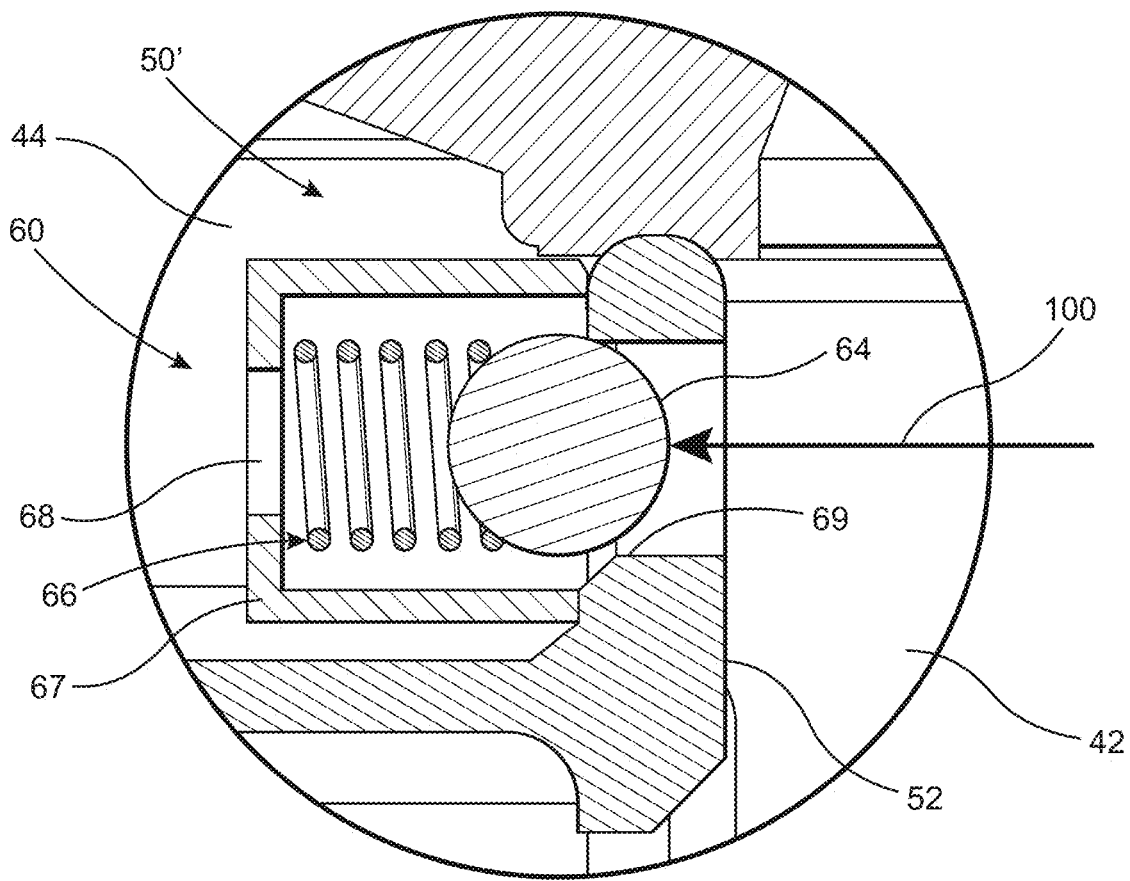
FIG. 5 is a sectional view of a pressure relief valve operatively associated with the embodiment of FIG. 4.

In yet another preferred embodiment as represented in FIGS. 4 and 5, the first passage 50 is eliminated and a different first passage 50' is substituted therefor. More specifically, the first passage 50' comprises and/or is associated with a pressure relief valve 60 including a housing 62, a biased valve member 64, and a biasing member 66 represented in detail in FIG. 5. The first passage 50' is disposed in fluid interconnecting relation between the primary chamber 42 and the interior of the reaction chamber 44. As such, the pressure relief valve 60, which at least partially defines the first passage 50', includes the valve element 64 normally biased in a closed orientation by the biasing spring or like biasing member 66. The first passage 50' is further defined by the valve housing 67 including oppositely disposed open ends 68 and 69, respectively disposed in direct fluid communication with the reaction chamber 44 and the primary chamber 42 respectively.

In use, the canister 14 is initially subjected to centrifugation to develop at least a first predetermined centrifugal force on the blood sample sufficient to cause a separation thereof into at least the aforementioned plasma segment and packed cell segment. Subsequent to separation of the blood sample, the aforementioned predetermined first or initial centrifugal force may be increased, as schematically represented by directional arrow 100, to the extent of forcing the ball valve or other valve element 64 against the biasing force of the biasing element 66 thereby opening the pressure relief valve 60 and the first passage 50'. Such opening will allow and/or direct the separated plasma segment from the primary chamber 42 through the valve housing 67 into the interior of the reaction chamber 44 during continuous centrifugation. It should be noted that while the valve element 64 is in the form of a ball, it may assume a variety of different sizes, configurations, etc. sufficient to establish a sealed engagement with the opening 69 in the barrier wall 52 and or valve housing 67.

It is emphasized that in one or more preferred embodiments the first passage 50 and/or 50' and the second passage including the one or more apertures 54 are disposed and structured to respectively establish an independent fluid communication between the primary chamber 42 and each of the reaction and cell chambers 44 and 46. Further, the reaction and cell chambers are not disposed in direct fluid communication with one another but only independently in fluid communication with the primary chamber 42.

Figure 6:
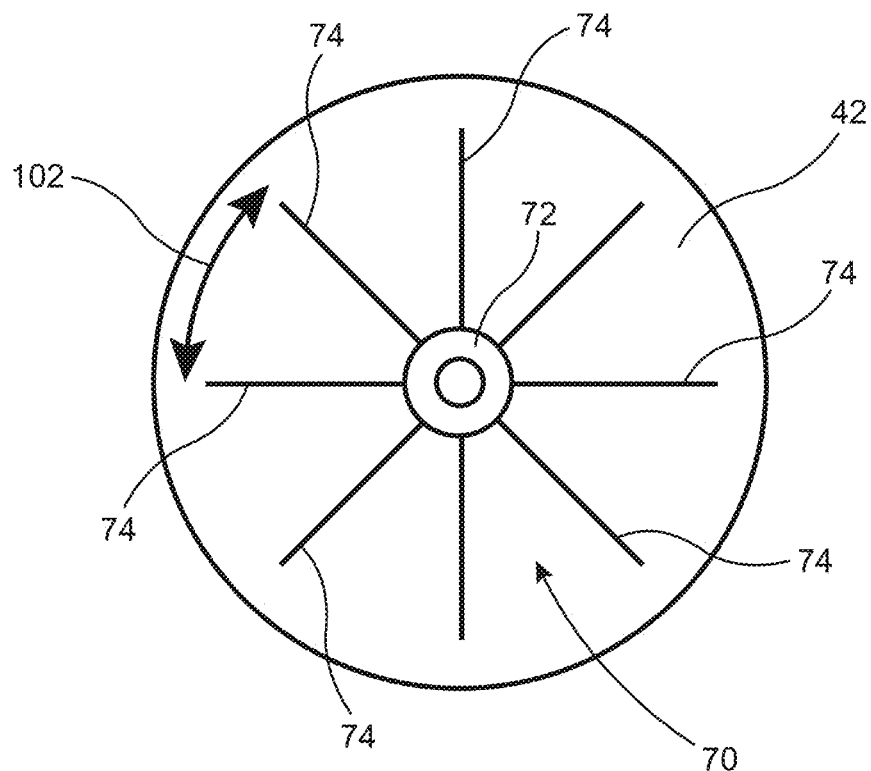
FIG. 6 is a detailed view of a stabilizing structure which may be operatively disposed within the interior of the primary chamber.
Figure 7:
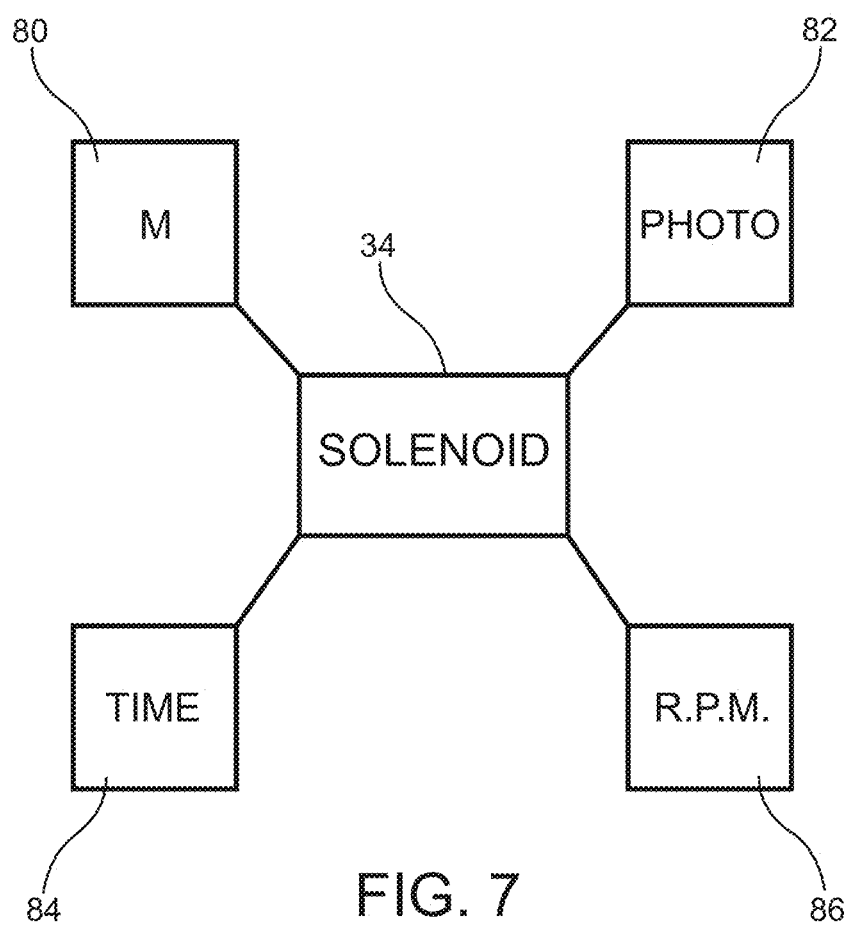
FIG. 7 is a schematic representation of a valve actuator assembly.

As represented in FIGS. 6, one or more embodiments of the present invention also contemplate the utilization of a stabilizing member or structure generally indicated as 70 disposed within the interior of the primary chamber 42. When so positioned, the stabilizing member or structure 70 movably interacts with the blood sample, at least initially, during centrifugation. The position and/or movement of the stabilizing member 70, schematically represented by directional arrow 102, may be accurately described as a substantially "free movement" because it may not be directly connected to interior portions of the primary chamber 42. Accordingly, the movable interaction with the stabilizing member 70 and the blood sample, during centrifugation, prohibits or restricts undesirable migration of the blood sample and a possible formation of disruptive pooling or collective grouping of the blood sample, to the extent that separation thereof into the plasma and packed cell segments is facilitated. Such an undesirable collection, grouping or pooling, etc. of the blood sample within the primary chamber 42 may be the result of vibration, initial uneven rotation of the canister 14 or other factors. The movable interaction of the stabilizer member 70 with the blood sample serves to substantially or at least partially more evenly distribute the blood sample within the primary chamber and thereby facilitate separation thereof into at least the plasma segment and the packed cell segment. In more specific terms, the stabilizing members 70 may include a hub 72 and at least one, but preferably a plurality of outwardly, radially extending fins or vanes 74. As such, the hub 72 and the one or more vanes 74 are cooperatively dimensioned and configured to movably interact with the blood sample, within the interior of the primary chamber 42, at least during centrifugation of the canister 14.

As indicated above and with primary reference to FIG. 6, the first passage 50 may be associated with a valve structure such as the valve 51 at least partially defined by the upper peripheral portion 40' of the primary chamber 42 and corresponding engaging under portions of the cover 25. As also indicated the valve 51 may be positioned between an open orientation and a closed orientation. Such positioning of the valve 51 may be accomplished by activation and/or operation of a valve actuator which at least partially includes the solenoid assembly 34. With further reference to FIG. 6, the valve 51 may be opened by a release or corresponding activation of the solenoid assembly 34 using a manual switch or activator 80. The manual switch 80 may be activated by a visual observation of the interior of the primary chamber 42, such as through apertures 13 formed in cap 28 (see FIG. 1), thereby providing a visual indication that separation of the supply blood sample has occurred. The valve 51 and accordingly the first passage 50 may then be manually opened in order to facilitate passage of the plasma segment from the interior of the primary chamber 42, through the passage 50 and into the interior of the reaction chamber 44.

With further reference to FIG. 6, the valve actuator, at least partially including the solenoid 34, may be operated/activated "automatically" by a determination of separation of the blood sample within the primary chamber 42. Such "automatic" actuation of the valve actuator may occur through the provision of a photo-sensor assembly 82 located in operative communication with the interior of the primary chamber 42 so as to detect any change in color, light, etc. which would in turn be indicative of the separation of the blood sample at least into the plasma segment. Further, the valve actuator may also include, a time-based activating assembly 84, which detects the length of time or duration of centrifugation. It can therefore be determined that after a certain period of time of centrifugation, the developed centrifugal force is sufficient to separate the blood sample at least into the plasma segment and the packed cell segment.

In cooperation therewith, a speed based (RPM sensor) activating assembly 86 may be included as part of the valve actuator. As such, when centrifuging or rotationally driving the canister 14 at a certain speed and possibly for at least a minimal duration, the blood sample will have been separated into at least the plasma and packed cell segments.

Accordingly, the manual or automatic operation/activation of the valve actuator, including the solenoid assembly 34, resulting in positioning of the valve structure 51 in an open orientation, is accomplished upon a determination that the initial blood sample has in fact segregated into at least the plasma segment and the packed cell segment. As further noted, the separation of the blood sample and the passage of the plasma segment and the packed cell segment out of the primary chamber occurs during centrifugation and is based on sufficient, predetermined centrifugal force being exerted on the cartridge 14.

With reference now to FIGS. 8-15, the present invention is illustrated in one or more additional embodiments. Specifically, with reference to FIG. 8, the invention is depicted as a device 100 comprising a base 110 connected to a rotational drive assembly 111, such as a centrifuge. As may be understood, the rotational drive assembly 111 may be structured and disposed to drive the base 110 at varying rotational speeds, thereby adjusting the centrifugal force to which the base 110, and any attachments thereto, is/are subjected. The base 110 includes a separation assembly which may comprise at least one separation chamber 120, such as a syringe, a cartridge, a vial, or other structure, and preferably a standard medical component. Further, the base includes a reaction assembly which may comprise at least one reaction chamber 130.

Figure 8:
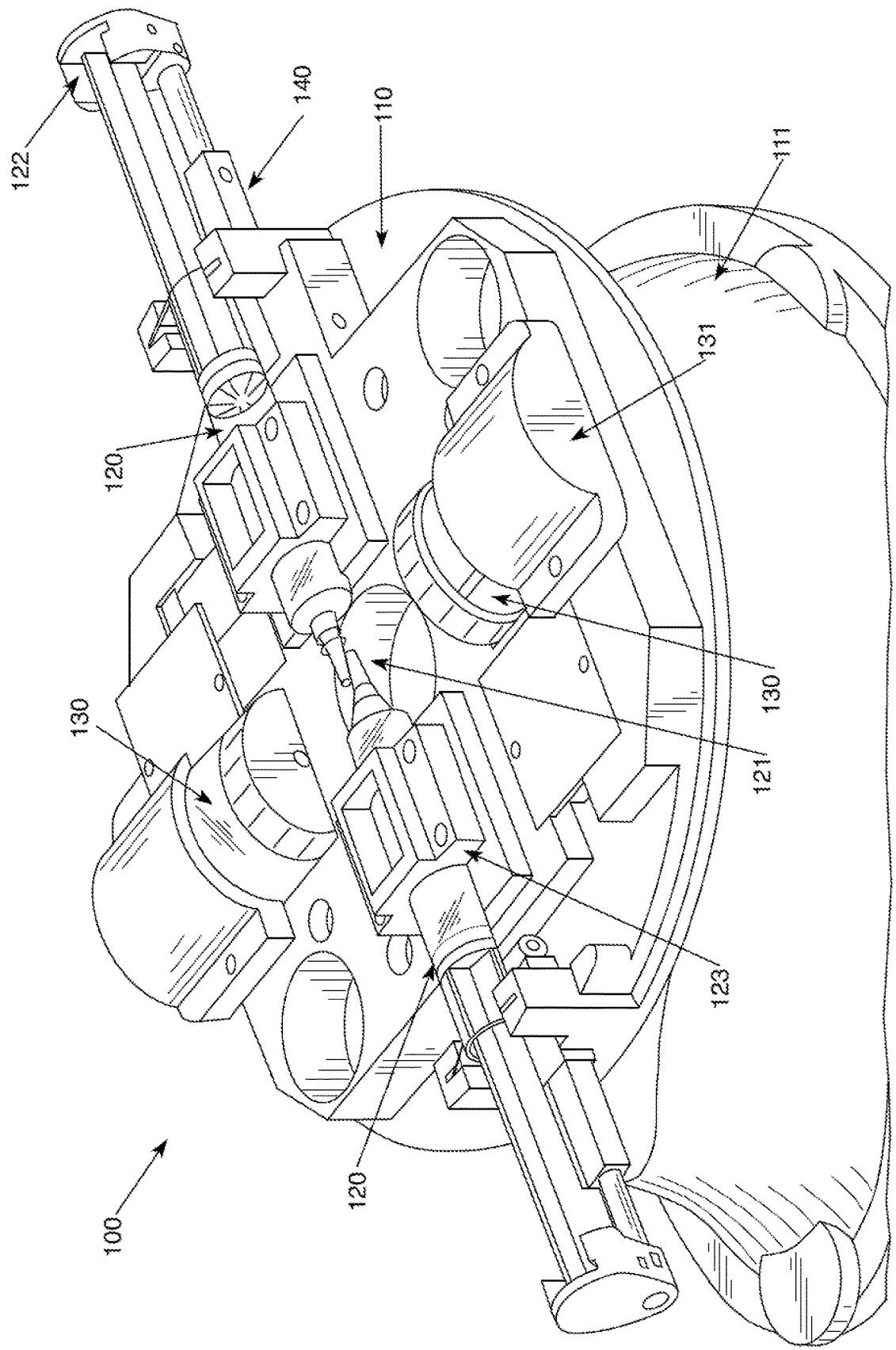
FIG. 8 is a perspective view of one embodiment of the present invention including a base, connected to a rotational drive assembly, with a separation assembly and a reaction assembly disposed thereon.

As may be seen, the separation chambers 120 and the reaction chambers 130 may be removably attached to the base 110 for the easy insertion and removal from the base 110. In such instances, and as depicted in FIG. 8, connection assemblies 123, 131 may secure the separation chambers 120 and reaction chambers 130 to the base 110 so they do not move during centrifugation. For example, such connection assemblies 123, 131 may comprise a fastener disposed to secure the separation chambers 120 and reaction chambers 130 to the base 110. As may be understood, further embodiments may employ alternative structural elements to fastenably secure the separation chamber(s) 120 and reaction chamber(s) 130 to the base 110.

Figure 9:
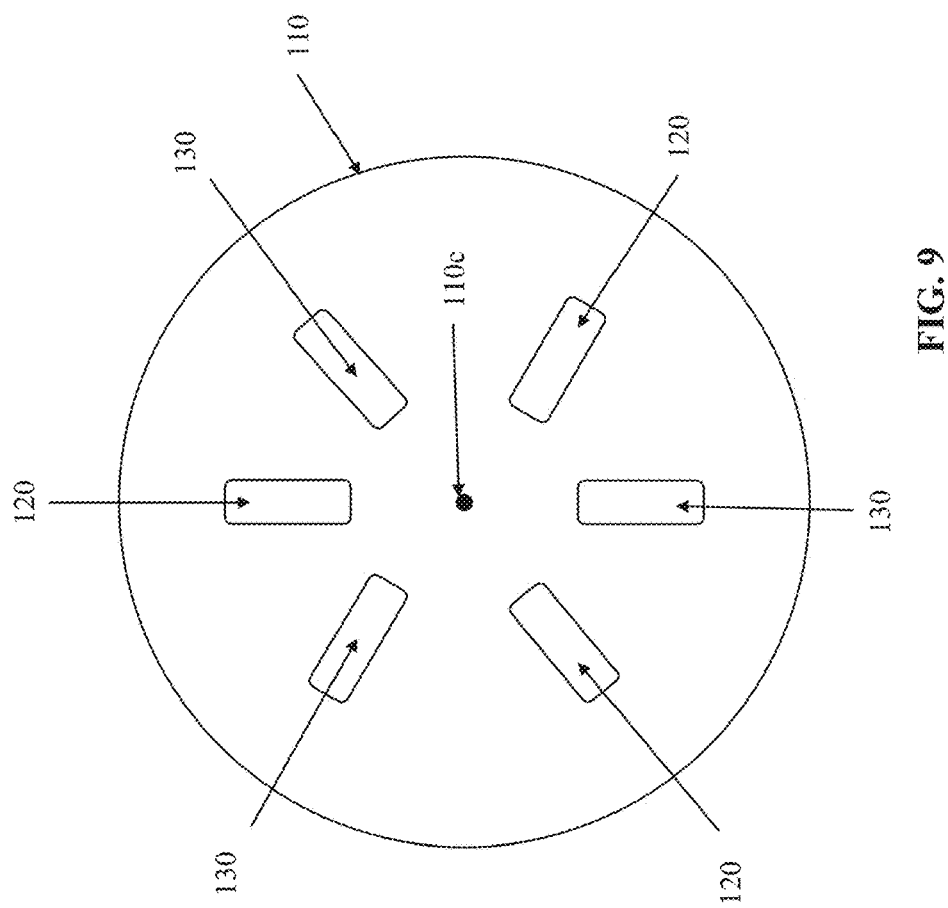
FIG. 9 is a schematic illustration of one embodiment of the present invention including a plurality of separation chambers and a plurality of reaction chambers disposed in counterbalancing relation to one another.

As set forth above, the base 110 may include at least one, and in some instances, a plurality of separation chambers 120 and/or reaction chambers 130. As may be understood, due to the application of centrifugal force to the base 110, the plurality of separation chambers 120 and/or reaction chambers 130 may preferably be disposed in a counterbalancing relation or orientation, such that the distributed weight from the separation chambers 120 and reaction chambers 130, as well as any further components disposed on the base 110, is disposed to maintain a center of mass located at the center of the base. For example, FIG. 9 depicts one embodiment of the present invention including three separation chambers 120 and three reaction chambers 130 so disposed in counterbalancing relation, wherein each separation chamber 120 is disposed in fluid communication with a distinct reaction chamber 130.

Figure 10:
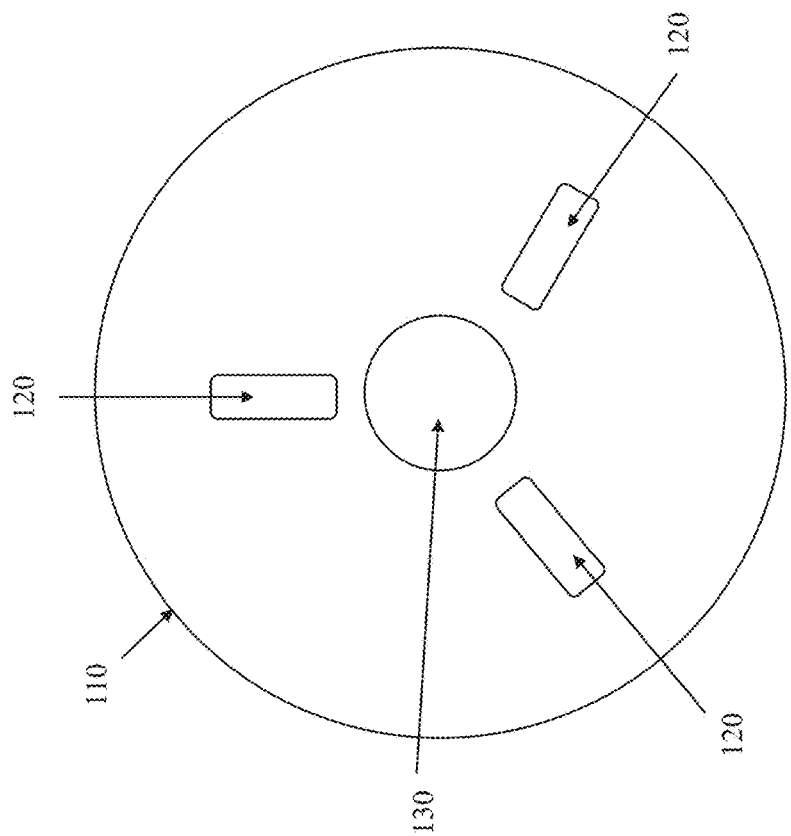
FIG. 10 is a schematic illustration of one embodiment of the present invention including a plurality of separation chambers and one reaction chamber disposed in counterbalancing relation to one another.

Likewise, FIG. 10 depicts one embodiment of the present invention including three separation chambers 120 and one reaction chamber 130 disposed in counterbalancing relation. As may be understood, various other embodiments featuring varying numbers of separation chambers 120 and varying numbers of reaction chambers 130 may be possible according to the disclosure herein.

As may be further understood, due to the transfer of fluid during the centrifugation process, the possibility of system imbalance remains. More specifically, there remains a possibility the device 100 may become imbalanced as a result of the dynamic movement of the fluid disposed therein. Accordingly, in at least some embodiments, such as those depicted in FIGS. 11 and 12, a balancing system 150 may be used in connection with the separation chamber(s) 120 and reaction chamber(s) 130 in order to maintain balance of the device. For instance, as can be seen in FIG. 11, in an embodiment featuring one separation chamber 120 and one reaction chamber 130, a balancing system 150 may be disposed on the base 110 and may comprise at least one movable weight 151 disposed to move along a predefined axis 151a. Accordingly, as fluid is transferred from the separation chamber 120 to the reaction chamber 130, the movable weight 151 may slide along the predefined axis 151a so as to counterbalance any occurring imbalance. Likewise, in a similar embodiment such as that depicted in FIG. 12, multiple balancing systems 150 may be utilized to effectively maintain the balance of the device 100. As may further be understood, and as previously stated, various alternative embodiments of the present invention may feature alternative structural embodiments as a part of the balancing system. For example, an actuation device 140 may be disposed on each separation chamber 120, as depicted in FIG. 8, wherein said actuation device 140 may individually drive fluid out of the separation chamber 120 to maintain balance of the device.

As previously stated, and with further reference to FIG. 8, the separation chambers 120 may be disposed on the base and structured for receipt of a blood sample. Upon at least an initial phase of centrifugation resulting from the driven rotation of the base 110 by the rotational drive assembly 111, the blood sample disposed within the separation chambers 120 may be separated into at least a plasma segment and a packed cell segment. Following the separation of the blood sample into the aforementioned segments, the plasma segment will accordingly be transferred from the separation chambers 120 to the reaction chambers 130 for additional processing into the fibrin foam or like fibrin product. Accordingly, in at least one embodiment, the plasma segment will travel from the separation chamber 120 to the separation chamber outlet 121, which may comprise a tip or a nozzle. Connected thereto may be a connector, such as a butterfly catheter, which may be disposed to transfer at least the plasma segment from the separation chamber 120 to the reaction chamber 130.

Still referring to FIG. 8, the fluid transfer of at least the plasma segment from the separation chamber 120 to the reaction chamber 130 may occur as a result of an actuation device 140 operatively disposed on or in connection with the separation chamber 120. For example, in at least one embodiment, the actuation device 140 may comprise a lead weight attached to the body of the separation chamber 120, which as noted above, may be a syringe. Accordingly, as centrifugal force is applied, the lead weight will be biased to draw the body of the separation chamber 120, in the case of a syringe, to the radial end of the separation chamber 120, which in the case of a syringe will comprise a plunger. As may be understood, in such an embodiment, the lead weight may comprise a heavier weight than that of the fluid disposed within the separation chamber 120 so as to overcome the force acting upon the plunger by the fluid. Accordingly, upon moving the body of the syringe to the plunger at sufficient force, fluid will be forced out of the separation chamber outlet 121, which may comprise a tip or a nozzle. Thus, in such a manner, it is possible to transfer the fluid purely as a result of the application of centrifugal force on the lead weight of the actuation device 140. Accordingly, instances of mechanical failure may be reduced due to the driving mechanism for fluid transfer consisting purely of the application of centrifugal force. Alternatively, as may be understood, the actuation device 140 may instead comprise a motor, whereby the fluid transfer of the plasma segment to the reaction chamber 130 may occur with or without the application of centrifugal force.

Further, in order to prevent the premature transfer of fluid, and to ensure enough pressure is employed upon said transfer of fluid, a mechanical safeguard, such as a shear pin or trip pin, may be employed in connection with the lead weight, whereby the lead weight will only be allowed to move in the radial direction upon the application of a certain amount of centrifugal force, which may be greater than the amount of centrifugal force applied when separating the blood sample. Accordingly, as may be understood, the device 100 may be disposed to increase the amount of centrifugal force applied to the base 110 only upon the occurrence of complete separation of the plasma segment and the packed cell segment. As stated previously, such full separation may be determined according to an individual patient's hematic profile, and may be set to occur after a given amount of time, a certain number of rotations, or any other applicable measurement determination.

Likewise, the actuation device 140 may alternatively comprise, in alternative embodiments, a spring assembly. Such a spring assembly may comprise, for example, a biasing element, a release clip, and a stopper. As may be understood, the biasing element may initially be compressed and biased to expand upon release. Upon said expansion, the base of the separation chamber 120, such as a syringe, may be driven towards the radial end 122 of the separation chamber, such as a plunger. Therefore, upon release of the biasing element by the release clip, at least the plasma segment may be transferred from the separation chamber 120 to the reaction chamber 130. As may be understood, the stopper may be used to ensure only the plasma segment is transferred to the reaction chamber 130. Further, as may be understood, the release clip may be set to trigger according to the patient's hematic profile, as previously discussed, or according to a manual input.

Additionally, certain embodiments of the present invention may lack an actuation device 140 for effectuating fluid transfer. As discussed previously, such embodiments may instead utilize a radial asymmetric orientation between the separation assembly 120 and the reaction assembly 130 to create a pressure differential resulting from the application of centrifugal force to the base 110.

For example, depicted in FIG. 13 is one embodiment of the present invention comprising a base 110 including two separation chambers 120 and two reaction chambers 130. As may be seen, the two separation chambers 120 are disposed in radial asymmetric orientation from the two reaction chambers 130. More specifically, the difference in radial position of the separation chambers 120 and the reaction chambers 130 from the axis of rotation of the base may operate to create a pressure differential sufficient to drive the fluid to an equal radial position in both the separation chambers 120 and the reaction chambers 130. Accordingly, in such an instance where the separation chamber radius 120r is shorter than the reaction chamber radius 130r, the application of centrifugal force to the base 110 will create a pressure differential between the separation chamber 120 and the reaction chamber 130, thereby resulting in a siphon effect. As may be understood, the siphon effect will force the fluid from the separation chambers 120 into the reaction chambers 130. Thus, a different amount of fluid may be transferred to the reaction chambers 130 dependent upon the radial asymmetric positions of the separation chambers 120 and the reaction chambers 130, and the actual circumference of each of the separation chambers 120 and reaction chambers 130.

As previously discussed, the siphon effect will first act upon the less dense plasma segment, thereby effectuating fluid transfer from the separation chambers 120 to the reaction chambers 130, as the denser packed cell segment will remain at the radial end 122 of the separation chamber 120 due to the application of centrifugal force. As may be understood, application of sufficient centrifugal force for a sufficient amount of time may cause the packed cell segment to likewise to begin to transfer out of the separation chamber 120.

Figure 14:
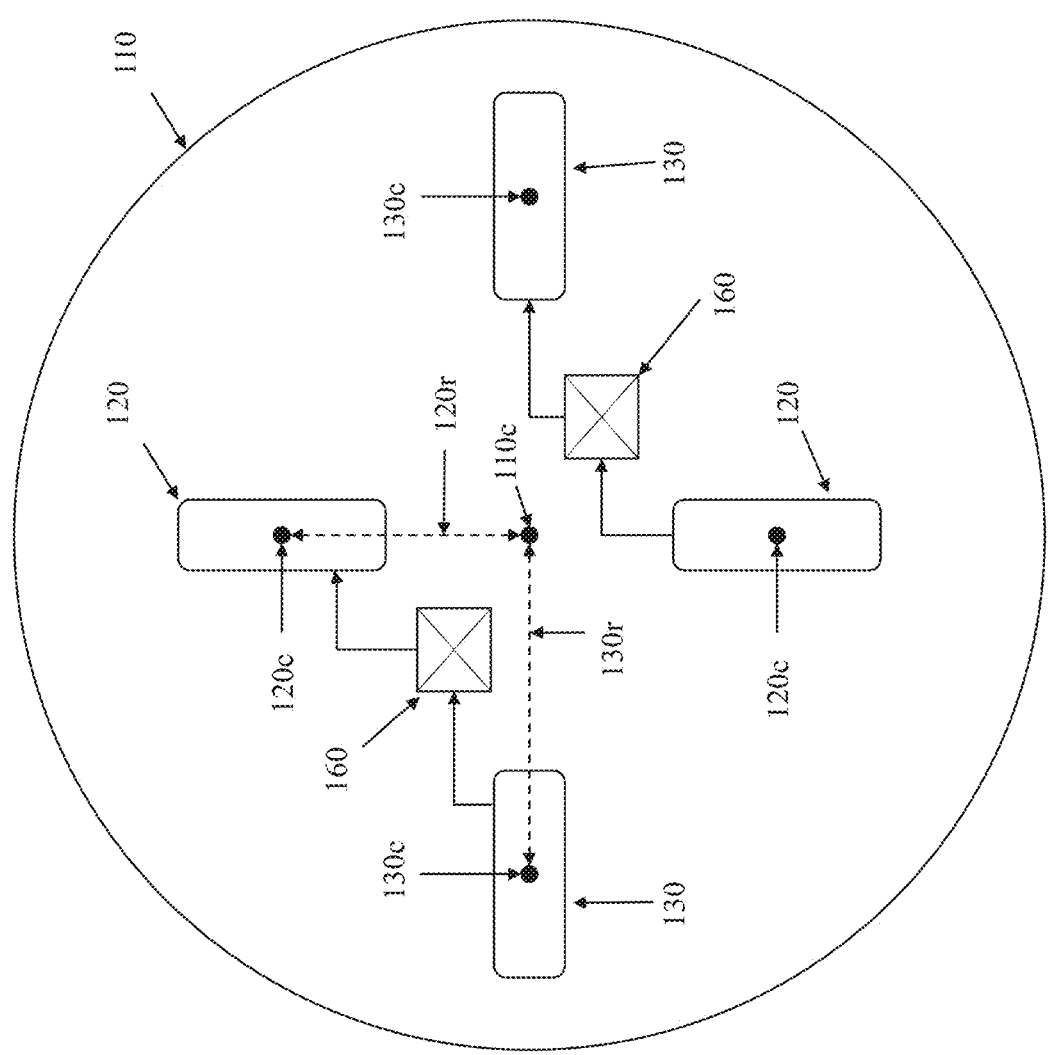

Accordingly, as may be seen in FIG. 14, in a further embodiment, at least one divider assembly 160 may be disposed between the separation chambers 120 and the reaction chambers 130. The divider assembly may comprise, for instance, a valve structure, such as a check valve or pressure burst disc, disposed to be in an open orientation, and therefore allow fluid transfer, upon the application of sufficient centrifugal force to meet the cracking pressure. Further, the valve structure may be disposed in connection with a filter, such as a red blood filter, which may be disposed to prevent the passage of red blood cells into the reaction chambers 130. Accordingly, such a divider assembly may be structured and disposed to only allow the plasma segment to enter into the reaction chambers 130.

As may be understood, and as previously stated, alternative embodiments may employ a variety of structural elements to prevent the passage of the packed cell segment into the reaction chamber 130. For example, in alternative embodiments, a mechanical stopper may be used to prevent the flow of excess fluid from exiting the separation assembly. In some instances, the appropriate volume of fluid to transfer may also be calculated according to the patient's known hematocrit, which may inform the physician as of the volumetric percentage of red blood cells in the patient's blood. Accordingly, an appropriate volume for fluid transfer may be specified according to such a calculation.

Moreover, in certain embodiments, a sensing device, such as a colorimetric sensor, laser, or image processing assembly, comprising at least a camera and an image processor, may be employed to prevent the passage of the packed cell segment into the reaction chamber. As may be understood, such a sensing device may be disposed at the separation chamber outlet 121, or between the separation chamber 120 and the reaction chamber 130, and be employed in connection with a logic board to monitor the separation assembly and the transfer of fluid therefrom. Due to the difference in color between the plasma segment, which is typically a clear, yellowish fluid, and the packed cell segment, which is typically a dark red fluid, such a sensing device may determine when the plasma segment has fully transferred to the reaction chamber 130, such as by colorimetry. At such time, the sensing device may issue a signal to operate associated mechanical structures, such as an actuator or mechanical stopper, to prevent the passage of the packed cell segment into the reaction chamber 130. Likewise, as may be understood, the sensing device may alternatively be used to detect the occurrence of the separation of the plasma segment and the packed cell segment from the blood sample.

As previously stated, subsequent to the separation of the blood sample and the transfer of the plasma segment to the reaction chamber 130, the plasma segment will be mixed, concurrent with the centrifugal force applied to the base, with air or an alternative gas and the reactant composition disposed therein for the formation of fibrin foam or other like fibrin product. Accordingly, upon mixture of the plasma segment with the aforementioned substances, a usable fibrin foam may be prepared. However, because fibrin foam or other like fibrin products may be characterized as a closed cell foam, meaning there will be no gas exchange with the fibrin foam's surroundings, various other procedural processes may be employed to further alter the chemical and physical properties of the fibrin foam or like fibrin product to more effectively tailor said fibrin foam for its particular application in the human body.

For instance, as previously stated, in one or more additional preferred embodiments the gas maintained or introduced into the reaction chamber 130 may be oxygen or air with an increased concentration of oxygen, in order to facilitate healing. The resulting fibrin foam or other fibrin product may be further enhanced by the addition of any other therapeutic medical gas or other agents such as, but not limited to, growth stimulants, hormones, cellular elements, bone, liver, skin, cartilage, chondroitin, platelets or other predetermined parts of the body with which the resulting fibrin foam product is intended for use. In addition, artificial organs may benefit from a fibrin foam matrix to add cellular support. Alternatively, as stated previously, a like medicinal component, such as an implant or a drug, may be disposed within the reaction chamber 130, such that the fibrin foam or like fibrin product may form around such implant or drug to act as a carrier of same upon the application of said fibrin foam or like fibrin product into a patient's body.

Further, in at least one embodiment, such as the one disclosed in FIG. 15, a fibrin foam or like fibrin product specifically tailored for application to specific areas of the human body, such as the ear or nose, may be effectively produced according to the disclosed method 200. As may be seen, a blood sample may first be disposed 201 within the separation chamber 120 and a centrifugal force may be applied to the base 110 to separate the blood sample 202 into the plasma segment and the packed cell segment. Subsequently, the plasma segment may be transferred 203*a* to the reaction chamber 130. Concurrent to the transfer of the plasma segment 203*a*, centrifugal force may be applied to create the fibrin foam or like fibrin product 203*b* in the reaction chamber 130.

In certain preferred embodiments, the reaction chamber 130 may be pressurized to a pressure greater than atmospheric pressure. As previously, stated, the reaction chamber 130 may be pressurized prior to the start of the method 200 disclosed herein. Alternatively, in other embodiments, the reaction chamber 130 may be pressurized when transferring the plasma segment to the reaction chamber 203*a* by applying greater centrifugal force to the base, or according to the force applied by an actuation device. More specifically, by applying greater force according to one of the aforementioned methods, air will flood into the reaction chamber 130, thereby increasing the pressure of the reaction chamber 130 beyond atmospheric pressure to, for instance, two atmospheres of pressure. Alternatively, as may be understood, the reaction chamber may be disposed at a pressure lower than atmospheric pressure to more closely imitate a vacuum. As may be understood, such lower pressure may instead create a denser fibrin foam with increased durability and longevity.

Next, prolonged and/or increased centrifugal force as at step 204 may be further applied to the device 100 in order to remove any excess water from the fibrin foam or like fibrin product. Next, the fibrin foam or like fibrin product may subsequently be removed from the reaction chamber 130. Accordingly, upon removal 205, and as stated previously, the gas bubbles disposed within the fibrin foam will expand in the case of greater pressure, or condense in the case of lower pressure, thereby decreasing or increasing the density of the fibrin foam or like fibrin product. Finally, the fibrin foam or like fibrin product may be dried 207 for a specified period of time.

As may be understood, the method 200 disclosed herein may be used to effectively create a fibrin foam or like fibrin product containing specific chemical and/or physical characteristics for application in specific regions of the human body, particularly the ear or nose. For instance, the fibrin foam or like fibrin product produced according to such a method may exhibit various physical characteristics such as variable density, variable thickness, greater elasticity, greater adhesiveness, and greater durability. Furthermore, if any additional medicinal components, such as therapeutic medical gasses or like agents, such as pure oxygen, implants, or other drugs are additionally introduced into the reaction chamber 130 prior to the creation of a fibrin foam or like fibrin product therein, such fibrin foam or like fibrin product may exhibit additional chemical attributes beneficial to its particular application or alternatively act as a carrier for such implants and/or drugs. For instance, in the event pure oxygen is used, the fibrin foam or like fibrin product may additionally help facilitate healing.

As may be further understood, the method 200 disclosed herein may additionally be altered in order to further tailor the chemical and/or physical properties of the produced fibrin foam or like fibrin product. For instance, by utilizing different amounts of pressure 203a in the reaction chamber 130, fibrin foams or like fibrin products of varying densities and/or thicknesses may be produced. Likewise, by altering the amount of water removed 205 by centrifugation, or by choosing not to dry 207 the fibrin foam or like fibrin product, varying elasticity levels and/or adhesiveness levels may be achieved.

Alternatively, the reaction chamber 130 may comprise a variation of different sizes and shapes. As may be understood, such embodiments may operate to create a fibrin foam or like fibrin product conforming to such shapes, thereby allowing for such fibrin foam or like fibrin products to be further tailored to specific applications in a patient's body.

Accordingly, as may be understood, the system, method, and included structural components as disclosed herein may allow for a device that may efficiently and effectively create specifically tailored fibrin foam or other like fibrin products while using standardized components and reducing incidences of device fatigue and/or failure resulting from problems such as system imbalance.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A device for the formation of fibrin foam therein, said device comprising:
   a base structured to be rotationally driven and including a separation assembly disposed thereon;
   said separation assembly structured for the receipt of a blood sample therein;
   said separation assembly structured to separate said blood sample into at least a plasma segment and a packed cell segment under centrifugal force concurrent to a driven rotation of said base;
   said base further comprising a reaction assembly;
   said reaction assembly disposed and cooperatively structured with said separation assembly for the receipt of said plasma segment therein subsequent to said separation of said blood sample;
   said separation assembly disposed in connection with at least one actuation device, said at least one actuation device structured and disposed to effectuate the fluid transfer of said plasma segment to said reaction assembly; and
   said reaction assembly further disposed to form a fibrin foam therein under said centrifugal force, concurrent to said driven rotation of said base.

2. The device of claim 1, wherein said base further comprises a divider assembly disposed between said separation assembly and said reaction assembly, said divider assembly structured and disposed to restrict said packed cell segment from entering said reaction assembly.

3. The device of claim 1, wherein said base further comprises at least one balancing system disposed maintain the rotational balance of said base.

4. The device of claim 1, wherein said separation assembly and said reaction assembly are disposed in rotational balancing relation to one another.

5. The device of claim 1, wherein said reaction assembly further comprises at least one reaction chamber containing at least a reactant composition disposed therein.

6. The device of claim 5, wherein said at least one reaction chamber further comprises at least one medicinal component.

7. The device of claim 1, wherein said separation assembly comprises at least separation chamber.

8. The device of claim 7, wherein said at least one actuation device comprises a lead weight disposed in connection with said at least one separation chamber.

* * * * *